United States Patent [19]

Sholder et al.

[11] Patent Number: 5,074,308

[45] Date of Patent: Dec. 24, 1991

[54] SYSTEM AND METHOD FOR RECOGNIZING PACEMAKER-MEDIATED TACHYCARDIA

[75] Inventors: Jason A. Sholder, Northridge; Stuart W. Buchanan, Saugus; Brian M. Mann, Beverly Hills, all of Calif.

[73] Assignee: Siemens-Pacesetter, Inc., Sylmar, Calif.

[21] Appl. No.: 588,226

[22] Filed: Sep. 26, 1990

[51] Int. Cl.$^5$ .............................................. A61N 1/37
[52] U.S. Cl. .............................. 128/697; 128/419 PT
[58] Field of Search ........... 128/697, 419 PG, 419 PT

[56] References Cited

U.S. PATENT DOCUMENTS

| | | | |
|---|---|---|---|
| 4,539,991 | 9/1985 | Boute et al. | 128/419 PG |
| 4,554,920 | 11/1985 | Baker, Jr. et al. | 128/419 PG |
| 4,554,921 | 11/1985 | Boute et al. | 128/419 PG |
| 4,569,350 | 2/1986 | Mumford et al. | 128/697 |
| 4,624,260 | 11/1986 | Baker, Jr. et al. | 128/419 PG |
| 4,712,555 | 12/1987 | Thornander et al. | 128/419 PG |
| 4,712,556 | 12/1987 | Baker, Jr. | 128/419 PG |
| 4,788,980 | 12/1988 | Mann et al. | 128/419.0 PG |
| 4,860,749 | 8/1989 | Lehmann | 128/419.0 PG |
| 4,944,298 | 7/1990 | Sholder | 128/419 PG |

OTHER PUBLICATIONS

Chorus 6003-6033 Implantable Dual-Chamber Pulse Generator *DDD MO Physician's Manual*, Published by ELA Medical, Inc. Minnetonka, MN (19).

*Primary Examiner*—William E. Kamm
*Attorney, Agent, or Firm*—Bryant R. Gold; Leslie S. Miller; Lisa P. Weinberg

[57] ABSTRACT

A pacemaker mediated tachycardia (PMT) is detected by circuitry within an implantable pacemaker. The PMT is detected by first detecting a tachycardia condition that includes a prescribed number of consecutive cardiac cycles having a rate faster than a prescribed rate. Each cardiac cycle of the tachycardia condition includes a natural atrial event, i.e., a P-wave, and a paced ventricular event, i.e., a V-pulse generated by a pacemaker. After the prescribed number of such cardiac cycles, e.g., two to ten, a P-V delay in a single cardiac cycle is modified by a first prescribed amount, e.g., 50 milliseconds. The time interval of a V-P interval associated with at least one cardiac cycle preceding the modified P-V delay is then compared to a V-P interval immediately following the modified P-V delay. Only if the difference between the V-P intervals thus measured is less than a second prescribed amount, e.g., 25 milliseconds, is a PMT indicated. If a PMT is indicated, a PMT termination regimen, e.g., extending PVARP, is automatically invoked by the pacemaker for a prescribed number of cardiac cycles, such as one or two cardiac cycles.

40 Claims, 12 Drawing Sheets

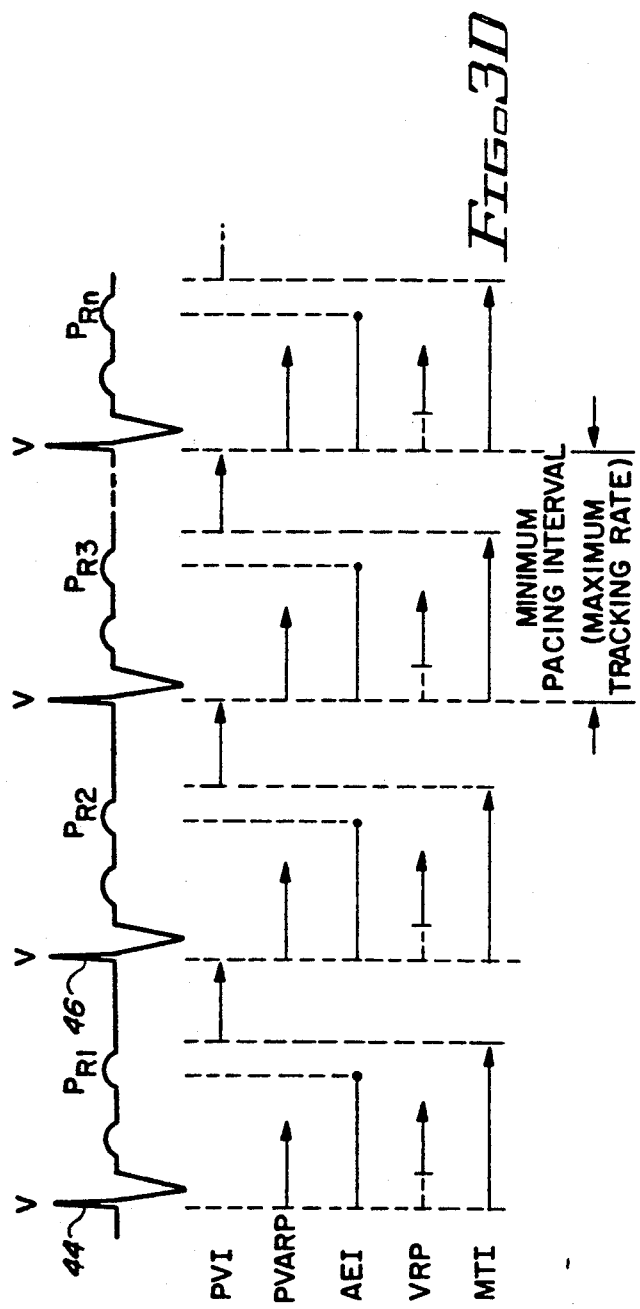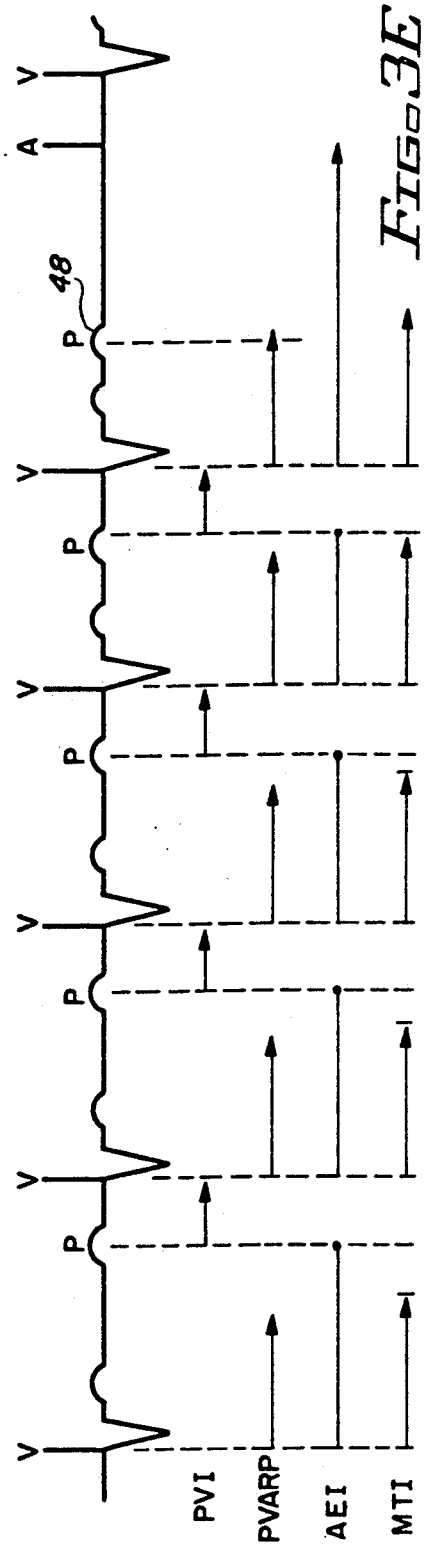

SYSTEM AND METHOD FOR RECOGNIZING PACEMAKER-MEDIATED TACHYCARDIA

BACKGROUND OF THE INVENTION

The present invention relates to cardiac pacemakers, and more particularly to implantable programmable cardiac pacemakers adapted to automatically detect and terminate the occurrence of a pacemaker-mediated tachycardia (PMT). Specifically, a pacemaker incorporating the present invention minimizes the likelihood that a PMT will be detected when a true PMT has not in fact occurred; and further assures that when a true PMT is detected, an appropriate PMT-terminating response is invoked.

In order to efficiently perform its function of a pump, the heart must maintain a natural AV synchrony. The term "AV synchrony" relates to the sequential timing relationship that exists between the contractions of the atria and the ventricles. In a given heart cycle or beat, the atria (A) contract prior to the ventricles (V) in accordance with a prescribed timing or synchronized relationship, hence the term "AV synchrony." These contractions are typically manifest or measured by sensing electrical signals or waves that are attendant with the depolarization of heart tissue, which depolarization immediately precedes (and for most purposes can be considered concurrent with) the contraction of the cardiac tissue. These signals or waves can be viewed on an electrocardiogram (ECG) and include a P-wave, representing the depolarization of the atria; the QRS-wave (sometimes referred to as a R-wave, the predominant wave of the group), representing the depolarization of the ventricles; and the T-wave, representing the repolarization of the ventricles. (It is noted that the atria also are repolarized, but this atrial repolarization occurs at approximately the same time as the depolarization of the ventricles; and any electrical signal generated by atrial repolarization is generally minute and masked out by the much larger QRS-wave on the ECG.)

Thus, it is the P-QRS-T cycle of waves that represent the natural AV synchrony of the heart. These waves, including the timing relationships that exist therebetween, are carefully studied and monitored through conventional ECG techniques whenever the operation and performance of the heart is being examined.

A pacemaker is a medical device that assists the heart in maintaining a desired AV synchrony by monitoring the atria and/or ventricles for the occurrence of P-waves and/or R-waves, and by producing stimulation pulses that are delivered to an appropriate chamber of the heart to cause that chamber to depolarize, and hence contract. (Because the main function of the pacemaker is to provide such stimulation pulses, a pacemaker is frequently referred to as a "pulse generator.") If for some reason the heart is unable to maintain its natural AV synchrony, a pacemaker is utilized to monitor the heart and to provide electrical stimulation pulses when it senses the heart is not maintaining a proper AV synchrony. A dual chamber pacemaker, for example, monitors both the right atrium and right ventricle. If it senses an atrial depolarization at appropriate times, no atrial stimulation pulse is generated. If it senses a ventricular depolarization within a prescribed time after the atrial depolarization, no ventricular stimulation pulse is generated. If however, it fails to sense either the atrial or ventricular depolarization within prescribed time periods, then stimulation pulses, frequently referred to as an A-pulse (if delivered to the atrium) and/or a V-pulse (if delivered to the ventricle), are generated and delivered to the appropriate chamber of the heart at an appropriate time in order to maintain the correct heart rhythm.

One of the problems that complicates the operation of a dual chamber pacemaker, i.e., one that is capable of sensing and/or pacing in both chambers of the heart, is "retrograde conduction". Retrograde conduction is a condition where the depolarization of the ventricles propagates backwards into the atria, causing the atria to depolarize prematurely. This atrial depolarization is manifest by the occurrence of a P-wave, frequently referred to as a "retrograde P-wave". A retrograde P-wave appears on the ECG substantially the same as a natural P-wave except that it occurs much too soon after a ventricular contraction. (A "natural" P-wave results from the natural AV synchrony of the heart as set by the heart's natural sinus rhythm, and is hereafter referred to as a "sinus" P-wave.) See U.S. Pat. No. 4,788,980 for a more thorough description of retrograde conduction.

Unfortunately, the pacemaker sensing circuits cannot readily distinguish between a retrograde P-wave and a sinus P-wave. A significant problem thus exists because once a P-wave is sensed, the pacemaker (depending upon its mode of operation) will typically generate a V-pulse a prescribed delay thereafter, referred to herein as the "P-V delay", unless an R-wave is sensed during the P-V delay. (It is noted that much of the literature refers to the P-V delay, as that term is used herein, as the "AV delay", or AVD. Further, some pacemakers employ one delay, a P-V delay, following a P-wave, and another slightly different delay, or AV delay, following an A-pulse. For purposes of the present invention, all such delays following an atrial event, whether an A-pulse or P-wave, are referred to herein as the "P-V delay".) If the sensed P-wave is a retrograde P-wave, an R-wave will not likely occur during this relatively short P-V delay time interval because the contraction of the ventricles just occurred prior to the retrograde P-wave. Thus, at the conclusion of the P-V delay, a V-pulse is generated by the pacemaker, causing the ventricles to again contract, which contraction causes another retrograde P-wave. This retrograde P-wave, in turn, causes another V-pulse to be generated after the P-V delay, causing the cycle to repeat, resulting in a pacemaker mediated tachycardia, or PMT. (A "tachycardia" is a very rapid rhythm or rate of the heart.)

Note that during a PMT, it is the pacemaker itself that causes or "mediates" the tachycardia by tracking each P-wave caused by the retrograde conduction, and providing a ventricular stimulation pulse a programmed P-V delay thereafter. The pacemaker thus provides the forward conduction path (from the atria to the ventricles) electronically by tracking each P-wave and generating a V-pulse (ventricular stimulation pulse) if no R-wave is sensed within a prescribed time thereafter (the programmed P-V delay). The reverse or backward conduction path (from the ventricles to the atria) is provided by retrograde conduction originating with the depolarization of the ventricles, which depolarization occurs as a result of the V-pulse. Thus, retrograde conduction passes the ventricular depolarization back to the atria, causing the atria to depolarize (resulting in a retrograde P-wave), and the process repeats.

Unfortunately, a PMT can be triggered by numerous events. The most common mechanism for triggering a PMT is a premature ventricular contraction, or PVC. A PVC, in turn, is not an uncommon occurrence for most mammalian hearts. A cough or a sneeze, for example, may cause a PVC. Unfortunately, for a patient having a dual chamber pacemaker that is set to operate in a mode that tracks P-waves and stimulates the ventricle, the occurrence of a single PVC can reset the pacemaker timing in a manner that allows the pacemaker to begin tracking retrograde P-waves, causing a PMT to occur. Such PMT, if allowed to continue for more than just a few cycles, seriously impacts the ability of the heart to efficiently perform its function of a pump. What is needed, therefore, is a system or method for accurately detecting the occurrence of a PMT, and quickly terminating such PMT once detected.

Unfortunately, detecting a PMT is not a simple matter. Not all rapid heart rates are caused by a PMT, as fast sinus heart rhythms may result from natural causes, many of which are beneficial. An attempt to break or terminate a fast sinus rhythm using PMT breaking techniques may not only be ineffectual, but may also be damaging and disruptive to the normal AV synchrony of the heart. Thus, there is a need in the art for a system and/or method that can reliably detect a true PMT from a fast sinus rhythm, or other non-PMT conditions.

One common technique used to prevent a PMT is to first detect a PVC, and assume that any rapid heart rate thereafter is a PMT. Thus, in order to prevent the occurrence of a PMT, it is known in the art for a pacemaker, upon the detection of a PVC, to revert to a DVI mode of operation for one cycle. (For an explanation of the various pacemaker modes, DDD, DDI, DVI, VVI, etc., see, e.g., U.S. Pat. No. 4,712,555.) This response, in effect, turns off the atrial sense amplifiers for one cycle. Hence, subsequent to the detection of the PVC, no P-waves can be sensed by the pacemaker because the electronic sense circuits are masked from sensing any atrial events, whether a retrograde event or a normal event. It is thus not possible for the pacemaker to generate a V-pulse one P-V delay after a retrograde P-wave, because the retrograde P-wave is not sensed. If the retrograde P-wave is not sensed, the occurrence of a PMT is prevented.

One problem with this approach of turning of the atrial sense amplifiers for one cycle is that if during the one cycle DVI response a normal sinus rhythm with spontaneous R-wave occurs, the PVC response remains on because the pacemaker interprets the spontaneous R-wave as another PVC. Thus, even though a possible PMT is prevented, the loss of normal P-wave tracking may occur because P-waves are masked by the response to the detected PVC, and any R-waves that are detected are interpreted as another PVC. Hence, the PVC response may become "stuck", as there is no way for it to terminate. Loss of P-wave tracking may occur from seconds to hours depending on the pacemaker's programmed rate settings and the patient's sinus rate.

Another response known in the art aimed at preventing a PVC from triggering a PMT is to extend the Post Ventricular Atrial Refractory Period (PVARP) by a prescribed amount, such as 480 msec. upon the detection of a PVC, thus masking retrograde conduction during this period of time. In addition, the atrial escape interval (VA delay) is fixed to a prescribed value, such as 830 msec., regardless of the programmed or sensor indicated rate (if a sensor is used, such as is the case in a rate-responsive pacemaker). See, e.g., U.S. Pat. No. 4,788,980. The difference between the selected PVARP value and the fixed VA delay, which difference is 350 msec. for the example given, advantageously allows a "window of time" during which a P-wave may be detected. This approach is an improvement over the DVI on PVC approach described above because the extended PVARP interval is sufficient to mask most retrograde conduction in the majority of patients, and P-waves not related to retrograde conduction can still be tracked. However, unless the sinus P-wave or other atrial event (e.g., an A-pulse) occurs during the window of time defined subsequent to the extended PVARP interval and prior to the termination of the VA delay (e.g., during the 350 msec. time period for the example times given above), the PVC response continues. Unfortunately, the PVC response can continue if P-waves fall within the extended PVARP interval (which will not be detected) followed by R-waves that cause the VA delay interval to be reset (with the R-waves being interpreted as PVCs). When this occurs, the PVC response thus causes a fixed atrial escape interval. In turn, this results in a slowdown of ventricular rate because the rate of pacing is made up of the AV delay (P-V delay) and the atrial escape interval (VA delay). Such a reduced ventricular rate may not meet the patient's then-existing physiological needs. What is needed, therefore, is a system that in its attempt to prevent a PMT does not slow down the patient's ventricular rate for a prolonged period.

Another technique known in the art for recognizing and breaking a PMT is used within the SYNCHRONY® pacemaker, manufactured by Siemens-Pacesetter, Sylmar, Calif. The SYNCHRONY® pacemaker utilizes both a maximum tracking rate (MTR) and a tachycardia recognition rate (TRR). The TRR is less than or equal to the MTR. Whenever the SYNCHRONY® pacemaker is pacing in the ventricle as a result of tracking P-waves and senses a rate that is higher than the TRR, the tachycardia termination routine is activated. This tachycardia termination routine operates as follows: Following the tenth or 127th beat at a rate greater than the TRR, the PVARP is extended to approximately 500 milliseconds. This is a sufficient extension to prevent most retrograde P-waves from being sensed, since most retrograde P-waves occur within 250 to 400 milliseconds after the contraction of the ventricle. Following the 500 millisecond PVARP, there is an approximately 350 millisecond alert period during which the pacemaker is able to sense a sinus P-wave. If no P-wave occurs by the end of this 350 millisecond alert period, the pacemaker logic circuits cause an atrial stimulation pulse, or A-pulse, to be generated. In either event (i.e., whether a P-wave is sensed or an A-pulse is generated) this should be the end of the PMT. This method of terminating a PMT is described more thoroughly in U.S. patent application Ser. No. 07/491,385, filed Mar. 9, 1990, which application is assigned to the same assigne as is the present application, and which application is incorporated herein by reference.

Unfortunately, while the PMT termination approach described above operates to terminate most PMTs, there are some situations where this is not the case. For example, if a ventricular beat (R-wave) is sensed before the sensed sinus P-wave or the delivered A-pulse, the pacemaker logic causes PVARP to remain extended for another cardiac cycle, thereby rendering the pacemaker incapable of sensing P-waves for an additional 500 millisecond period. This extended PVARP of 500 milliseconds continues for each cardiac cycle where an R-wave is sensed before a P-wave. Thus, as R-waves continue to be sensed, it is possible for PVARP to be continually extended, thereby effectively eliminating any capability of the pacemaker to sense and track P-waves (because P-waves cannot be sensed during the 500 milliseconds after a ventricular contraction). What is needed, therefore, is an improved response to a sensed PMT that is not extended indefinitely.

An additional problem is created whenever PVARP is extended when the pacemaker is a rate-responsive pacemaker. In a rate-responsive pacemaker, the pacing rate is controlled by a separate activity sensor that detects patient activity (or some other parameter indicative of the need to adjust the heart rate). If such an activity sensor is employed, and if the extended PVARP response continuously repeats (i.e., R-waves are sensed but P-waves are not), then, in effect, the activity sensor is disabled. For example, if the P-V delay is 150 msec., then the rate during an extended PVARP response would be, using the same numbers presented above, 150 msec. + 850 msec. = 1000 msec., or about 60 beats per minute. Any sinus P-waves falling within the extended PVARP interval are not sensed, hence the extended PVARP response remains on when accompanied by detected R-waves prior to the end of the VA delay. Thus, sensor controlled rates are prevented from being effective since the extended PVARP interval controls the atrial escape interval. In other words, since the extended PVARP response slows the ventricular rate down from a higher sensor controlled rate, it is more likely that a sinus rhythm will keep the extended PVARP response on, thereby causing a slower ventricular rate, which slower rate may be undesirable when the patient may be in need of increased cardiac output during activity. Hence, multiple extensions of PVARP upon the detection of a PMT may be an inappropriate response for a sensor-driven rate responsive pacer. What is needed, rather, is a technique or method for clearly recognizing and responding to the occurrence of a PMT, regardless of whether the pacemaker responsible for the PMT is a rate-responsive pacemaker or a fixed (programmable) rate pacemaker.

It is thus evident that there is a need in the art for a system that recognizes only true PMTs, and that does not condition its recognition of a true PMT upon a P-wave rate that is simply higher than a rate threshold (TRR), since non-PMT events, such as fast sinus rates or atrial tachycardias, can mimic a true PMT. A true PMT is defined as a cardiac cycle that includes a V-pulse followed by a retrograde P-wave, which retrograde P-wave triggers a subsequent V-pulse, followed by another retrograde P-wave, and so on, with the forward atrial-to-ventricular path in this cycle always being provided through the pacemaker, and the rearward ventricular-to-atrial path being provided through retrograde conduction, which retrograde conduction time is very stable, and thus P-V and P-P times are also stable. What is further needed is a system that responds to the detection of a true PMT by invoking a PMT-terminating regimen calculated to terminate the PMT as rapidly as possible without any possibility of indefinitely slowing the heart rate down to dangerously low rates.

The present invention advantageously addresses the above and other needs.

SUMMARY OF THE INVENTION

The present invention advantageously recognizes a true PMT by monitoring the time interval, either directly or indirectly, between successive V-pulses and P-waves of a rapidly beating heart. This time interval is referred to as the V-P interval. The V-P interval forms a portion of every cardiac cycle of a potential PMT. During a true PMT, the V-P interval is largely determined by the retrograde conduction time, and is substantially constant for a given cardiac cycle rate. In contrast, in a rapid sinus rate (non-PMT), the V-P interval varies from cycle to cycle by a noticeable amount.

In accordance with one aspect of the invention, a true PMT is detected by first looking for a sequence of rapid cardiac cycles, each cycle including the essential ingredients of a PMT, i.e., V-pulse preceded by a P-wave. If the sequence of cardiac cycles exceeds a prescribed rate, then a potential PMT exists. To determine if a true PMT exists, the length of a single cardiac cycle (or a small group of cardiac cycles) is changed, i.e., increased or decreased, on a one time basis. This is preferably done by modifying the P-V delay set by the pacemaker for the single cardiac cycle (or small group of cardiac cycles) that is modified. The V-P interval immediately preceding the modified P-V delay is then measured and compared to the V-P interval immediately following the modified P-V delay. If there is no significant change or difference between the V-P intervals thus monitored, a PMT is indicated. If there is a significant change or difference, a PMT is not indicated.

The sequence of rapid cardiac cycles is readily detected using the pacemaker's existing sensing and monitoring circuits to look for the prescribed sequence of events, i.e., a P-wave followed by a V-pulse, and to monitor the time interval (i.e., rate) between successive V-pulses. A comparator circuit, or equivalent, compares the time interval thus measured relative to a reference time interval. This reference time interval defines a threshold rate which the monitored rate must exceed for the cardiac cycles to be considered sufficiently rapid to comprise a potential PMT. To assure that a truly rapid heart rate exists, a prescribed number of successive cardiac cycles, e.g., two to ten, each having a V-V interval less than the reference time interval (and hence each having a rate greater than the threshold rate), must be detected. Alternatively, an average V-V time interval of a prescribed number of cardiac cycles less than the reference time interval may be used to indicate the fast cardiac cycle condition.

The length of the single cardiac cycle (or small group of cardiac cycles) is preferably changed by changing the P-V delay. The P-V delay, in turn, is modified using the same basic pacemaker circuits used to programmably change the P-V delay. The only difference is that the pacemaker control circuits cause this change to occur automatically for one cycle (or a small number of cycles) whenever the requisite number of prescribed cardiac cycles have occurred at a fast rate. The amount of the P-V delay change may be programmably set to any desired value, e.g., ±50 msec.

In accordance with another aspect of the invention, there is provided a system and method for detecting whether a detected fast cardiac cycle condition represents a true PMT, or simply a rapid sinus rate. In a preferred embodiment, this detection system and method involves extending the P-V interval set by the pacemaker for a single cardiac cycle. The V-P interval immediately preceding the extended P-V interval is measured, as is the V-P interval immediately following the extended P-V interval. If these V-P intervals are substantially the same, a PMT is indicated.

The preferred manner of measuring the V-P intervals immediately preceding and following the extended P-V interval is to measure the duration of overlapping cardiac cycles, each including the extended P-V interval. A first of these overlapping cycles, measured between successive V-pulses, begins with a first V-pulse, is followed by a first P-wave, and concludes with a second V-pulse. The extended P-V interval between the time interval between the first wave and the second V-pulse. The V-P interval immediately preceding the extended P-V interval comprises the time interval between the first V-pulse and the first P-wave. A second of the overlapping cycles, measured between successive P-waves, begins with the first P-wave, is followed by the second V-pulse, and concludes with a second P-wave. The extended P-V interval comprises the time interval between the first P-wave and the second V-pulse. The V-P interval immediately following the extended P-V interval comprises the time interval between the second V-pulse and the second P-wave.

When a true PMT is present, the V-P interval is primarily determined by the retrograde conduction time, which time is not substantially affected by extending the P-V interval for one (or for a small number) of cardiac cycles. When a true PMT is not present, the V-P interval is not determined by the retrograde conduction time, and the V-P interval immediately following the extended P-V interval is substantially affected by extending the P-V interval. Hence, if the first overlapping cardiac cycle, which may be referred to as the V-V cycle (measured between the first and second V-pulses, and includes the V-P interval immediately preceding the extended P-V interval), is substantially the same as the second overlapping cardiac cycle, which may be referred to as the P-P cycle (measured between the first and second P-wave, and includes the V-P interval immediately following the extended P-V interval), where both the V-V cycle and the P-P cycle include the extended P-V interval, then that indicates that the V-P interval immediately preceding the extended P-V interval must be substantially the same as the V-P interval immediately following the extended P-V interval. Hence, a V-V cycle having a duration substantially the same as the duration of an overlapping P-P cycle under these conditions indicates that a PMT exists. In contrast, a V-V cycle having a duration that is not substantially the same as the duration of an overlapping P-P cycle under these conditions indicates that a PMT does not exist.

In accordance with another aspect of the invention, a PMT termination regimen is automatically triggered upon the detection of a PMT. This regimen is calculated to quickly terminate the PMT, e.g., within one cardiac cycle. This regimen is initially invoked for one cycle only. However, if the PMT is not successfully terminated by the initial invoking of the PMT-terminating regimen, then it may be selectively invoked for two or more consecutive cardiac cycles upon the second or subsequent successive detections of a PMT.

It is a feature of the present invention to provide a system or method for accurately detecting the occurrence of a PMT, and quickly terminating such PMT once detected.

It is another feature of the invention to provide such a system and/or method that can reliably detect a true PMT from other fast sinus rhythms (non-PMT conditions).

It is an additional feature of the invention to provide a safe and effectual PMT response to a sensed PMT that is not extended indefinitely. In accordance with such feature, the detection of a true PMT invokes a PMT-terminating regimen calculated to terminate the PMT as rapidly as possible without any possibility of indefinitely slowing the heart rate down to dangerously low rates.

It is yet a further feature of the invention to provide a technique or method for clearly recognizing and responding to the occurrence of a true PMT without interfering with the normal operation of the pacemaker. Such a technique thus allows the pacemaker to perform its intended function (e.g., of providing stimulation pulses on demand) regardless of whether the pacemaker responsible for the PMT is a rate-responsive pacemaker or a fixed (programmable) rate pacemaker.

BRIEF DESCRIPTION OF THE DRAWINGS

The above and other aspects, features and advantages of the present invention will be more apparent from the following more particular description thereof, presented in conjunction with the following drawings wherein:

FIG. 3D is a composite timing diagram illustrating a PMT at the maximum tracking rate (MTR) of the pacemaker;

FIG. 3E is a composite timing diagram illustrating a sinus rate greater than the MTR of the pacemaker;

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

In order to better understand the present invention, it will first be helpful to review some basic cardiac physiology, and the manner by which a pacemaker assists a mammalian heart in maintaining a desired AV synchrony. Accordingly, reference is made to FIG. 1, where there is shown a typical ECG-type waveform illustrating a normal cardiac cycle of a heart. Such waveforms may be obtained using conventional skin-electrode ECG techniques. Alternatively, intracardiac ECG features of modern pacemakers provide similar ECG information through the use of the telemetry features of such pacemakers.

Figure 1:
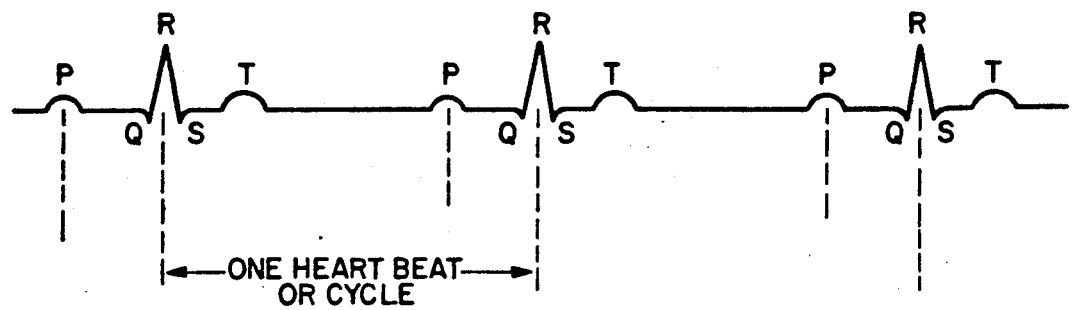
FIG. 1 is a typical ECG-type waveform illustrating the normal AV synchrony of the heart.

Beginning at the left of the waveform of FIG. 1, there is shown a P-wave. This P-wave represents the electrical activity coincident with the depolarization of the atria of the heart. Depolarization of the atria is accompanied by contraction of the atria, thereby allowing blood to be pushed from the atria into the ventricles of the heart. While those skilled in the art will recognize that depolarization and contraction are not necessarily simultaneous events, they will be assumed to be simultaneous events for purposes of this patent application, and the terms "depolarization" and/or "contraction" are meant to be synonymous.

A short time subsequent to the generation of the P-wave, the QRS complex appears, representing the depolarization of the ventricles. The time period between the P-wave and the QRS wave (often referred to as simply an R-wave) is an important time interval in the operation of the heart because it represents the time needed for the blood to flow from the atria into the ventricles. The R-wave is followed by a T-wave, which wave represents the electrical activity associated with the depolarization of the ventricles.

As known to those skilled in the art, the ventricles do most of the work in pumping the blood throughout the body. Typically, one heart beat or heart cycle is measured as the time interval between succeeding R-waves, simply because the R-wave typically represents the easiest of the waves to identify and measure. A heart beat may, of course, be measured relative to any point within the heart cycle, such as between succeeding T-waves or P-waves.

A certain rhythm or synchrony must occur if the heart is to perform its function of a pump efficiently. That is, the depolarization of the atria, represented by the P-wave, must be followed a short time thereafter by the depolarization of the ventricles, represented by the R-wave. After a sufficient delay, the atria must again depolarize, followed by the depolarization of the ventricles. If the depolarization of the atria or ventricles do not occur naturally, then a pacemaker may be employed to provide stimulation pulses to these respective heart chambers in order to trigger the required depolarization/contraction at the appropriate time periods of the heart cycle.

Figure 2:
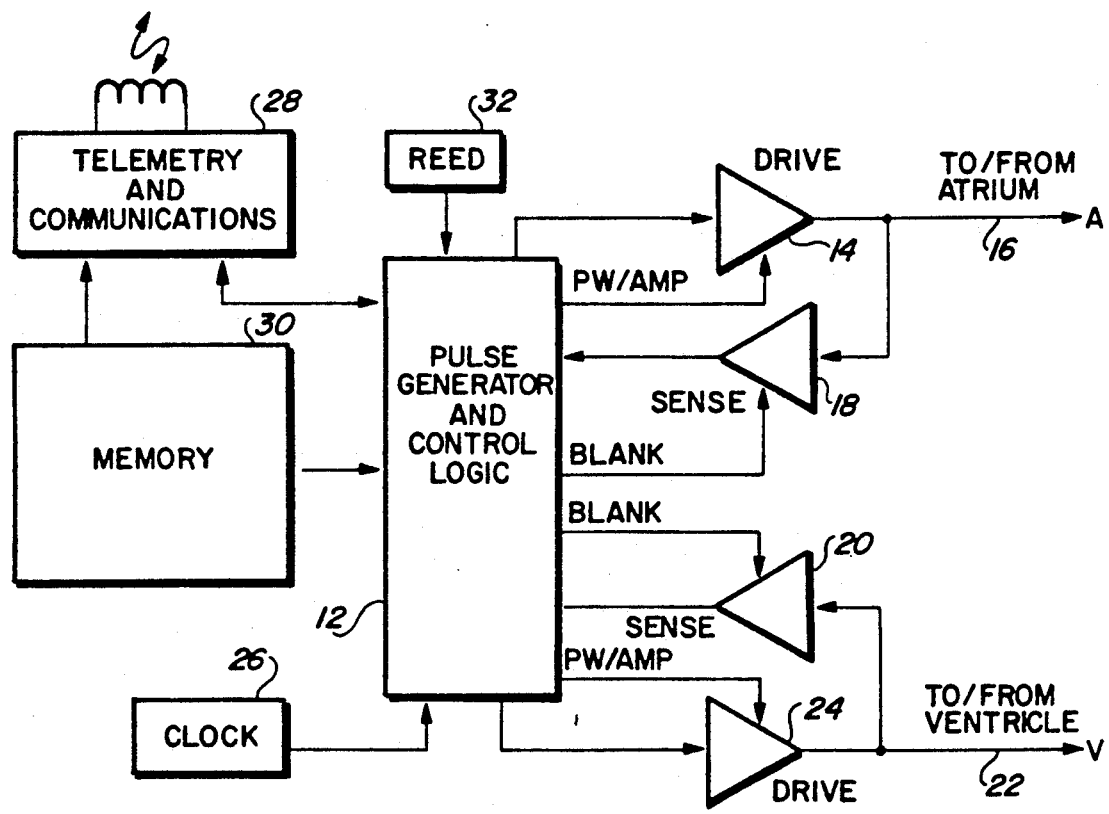
FIG. 2 is a block diagram of an implantable, programmable, dual-chamber pacemaker.

Referring next to FIG. 2, a block diagram of a typical atrial tracking dual-chamber pacemaker 10 is illustrated. As explained below, the circuitry shown in FIG. 2 may be used to carry out the PMT recognition and termination method of the present invention. In FIG. 2, Pulse Generator and Control Logic 12 generates the appropriate timing signals and sequences to enable stimulation pulses to be generated and delivered to the heart. Stimulation pulses are delivered to the right atrium of a heart (not shown) through an atrial drive amplifier 14 and an atrial lead or conductor 16. This same atrial lead 16 is connected to an atrial sense amplifier 18. This sense amplifier 18 monitors the electrical activity of the atrium to determine if a sinus P-wave, representing the natural depolarization of the atrium, has occurred. If such sinus atrial activity is sensed, then Pulse Generator and Control Logic 12 inhibits the stimulation pulse provided to the drive amplifier 14 and provides for a ventricular stimulus after a predetermined time period (referred to as the P-V delay). However, if a sinus P-wave has not been sensed after a prescribed period of time, typically referred to as the atrial escape interval, then the Pulse Generator and Control Logic 12 delivers a stimulation pulse ("A-pulse") through the drive amplifier 14 to the atrium over lead 16. The pulse width and amplitude of this stimulation pulse are controlled by the Pulse Generator and Control Logic 12.

In a similar manner, the Pulse Generator and Control Logic 12 senses the electrical activity occurring in the right ventricle of the heart through a sense amplifier 20 connected to a ventricular lead 22. If naturally occurring ventricular electrical activity is not sensed within an appropriate ventricular escape interval, then the Pulse Generator and Control Logic 12 generates a ventricular stimulation pulse ("V-pulse") of a prescribed pulse width and amplitude, delivered through the drive amplifier 24, in order to cause the desired ventricular contraction. If naturally occurring ventricular electrical activity is sensed, i.e., if an R-wave is sensed, then the Pulse Generator and Control Logic 12 inhibits the pulse provided to the drive amplifier 24 and resets the pacemaker timing logic within the Pulse Generator and Control Logic 12.

Clock circuitry 26 provides the basic clock signals or timing signals from which the Pulse Generator and Control Logic 12 operates. Telemetry and communications circuitry 28 provides a means whereby information can be telemetered to and from the implanted pacemaker. Control information that varies the basic escape intervals of the pacemaker, for example, may be received through the telemetry and communications circuitry 28 and stored in a memory 30, as may control information that sets the desired pulse width and/or amplitude of the stimulatinq pulse, as well as other control parameters used within the pacemaker. Such control information may also be passed directly to the Pulse Generator and Control Logic 12, if desired. Similarly, electrical activity of the heart, as sensed through the sense amplifiers 18 and 20, can be telemetered external to the pacemaker through the telemetry and communications circuitry 28, thereby allowing an attending physician or other medical personnel, e.g., cardiologist, to monitor the activity of the heart without the use of external skin electrodes.

A magnetic reed switch 32 is also typically employed with implanted pacemakers in order to control the programmable functions of the device. With a suitable programming apparatus in place, the reed switch 32 is closed and the attending physician or cardiologist can effectuate any desired changes in the operation of the pacemaker by sending appropriate control signals and commands over the telemetry and communications circuitry 28. Without the appropriate programming apparatus, the reed switch 32 remains open, and the telemetry and communications circuitry 28 is not operable.

Figure 3A:
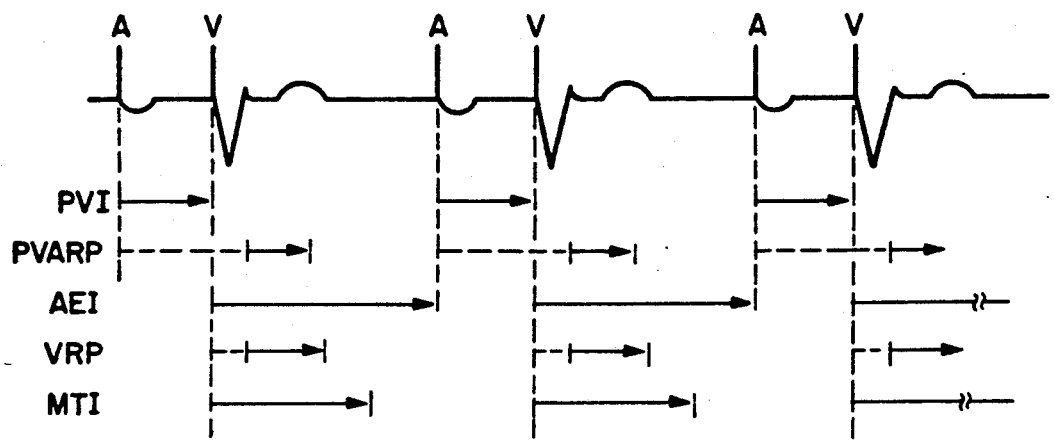
FIG. 3A is a composite timing diagram illustrating how the AV synchrony of the heart is maintained when both atrial and ventricular stimulation pulses are provided to the heart by a dual-chamber pacemaker.

Referring next to FIG. 3A, a composite timing diagram illustrating the operation of a typical demand-type, dual-chamber pacemaker, is illustrated. In this and other timing diagrams used herein, the stimulation pulses generated by the pacemaker are illustrated as a narrow spike labeled with either an A (for an atrial stimulation pulse) or a V (for a ventricular stimulation pulse). Further, unless otherwise indicated, the response of the heart to an applied stimulation pulse is indicated in the figures as having an opposite polarity from that shown in FIG. 1. (FIG. 1 depicts the natural or sinus rhythm of the heart, and thus the heart responds without the application of a stimulation pulse.) This is done to clearly distinguish in the figures naturally occurring events of the heart from pacer-induced (paced) events.

Included in the timing diagram of FIG. 3A are representations of the various timing intervals that are generated by the control logic 12 (FIG. 2). Many of these time intervals are programmable, meaning that the length of such intervals can be varied by sending appropriate control signals over the telemetry and communications circuitry 28 to the memory circuits 30 of FIG. 2. As known to those skilled in the electronic arts, there are numerous methods and techniques through which a time interval can be varied. One such technique involves loading an appropriate data word into a prescribed memory location, which data word is subsequently loaded into an appropriate counter of the control logic 12. A basic clock signal is then used to clock this counter until the desired count is reached, at which time a terminal count signal (frequently termed a "timed out" signal) is generated to indicate the end of the desired time interval. By merely changing the value of the data word that is loaded into memory, and knowing or controlling the rate of the clock signal, the length of the time interval can be varied or programmed to a desired value. Analog techniques may also be used to generate a time interval, such as are used within commercially available, or equivalent, one-shot multivibrator circuits.

The time intervals shown in the timing diagrams that follow are indicated by a horizontal line. If the time interval has "timed out" —that is, if it has reached its terminal count—an arrowhead is placed on the horizontal line, pointing to the point in time at which the time interval terminates. (The horizontal axis of the timing diagrams represents the time axis.) It is noted that the timing drawings are not necessarily drawn to scale, nor with linear horizontal or vertical axes. It is also noted that some cardiac events, such as the T-wave, may be omitted from some of the timing diagrams. If a sensed electrical event occurs prior to the termination of a given interval, which event inhibits the generation of a stimulation pulse (or alters some other operation of the pacemaker) then a dot is placed on the horizontal line indicating the point in time at which the sensed event terminates or resets that particular interval.

Shown in FIG. 3A are five basic time intervals. These five time intervals are not the only time intervals defined by the Control Logic 12 and used in the operation of a pacemaker, but are some of the most pertinent time intervals utilized by the present invention. These five intervals are: (1) the P-V interval, or PVI, representing the desired time interval between atrial depolarization and ventricular depolarization; (2) the post ventricular atrial refractory period, or PVARP, representing the time interval subsequent to a ventricular event during which the atrial sensing circuits are disabled; (3) the atrial escape interval, or AEI, representing the time interval after which, in the absence of naturally occurring atrial activity during such interval, an A-pulse is generated and delivered to the atrium (sometimes also referred to as the VA interval); (4) the ventricular refractory period, or VRP, representing the interval during which the ventricular sense amplifier 20 (FIG. 2) is disabled; and (5) the maximum tracking interval, or MTI, representing the interval that defines the maximum tracking rate at which the pacemaker may operate. (The intervals MTI+PVI thus define the shortest possible time period of a pacemaker-defined cardiac cycle, and hence, the maximum possible paced ventricular rate.)

With the above basic timing intervals thus defined, the following description of FIGS. 3A-3E will be presented. As indicated previously, FIG. 3A illustrates how a pacemaker is used to maintain a desired rhythm or synchrony of the heart. For the situation shown in FIG. 3A, it is assumed that the heart cannot provide its own atrial or ventricular contractions at a suitable rate, and that the pacemaker must therefore provide the stimulation pulses required to maintain the desired heart rate. Accordingly, an atrial stimulation pulse "A" is provided in order to invoke a contraction of the atria. This event triggers the P-V interval, PVI. At the termination of the PVI, a ventricular stimulation pulse, V, is generated and applied to the heart. This stimulation pulse causes the ventricle to contract, as indicated by the inverted R-wave. The generation of the ventricular stimulation pulse, or V-pulse, also triggers the beginning of the post ventricular atrial refractory period, or PVARP; the atrial escape interval, or AEI; the ventricular refractory period, or VRP; and the maximum tracking interval, or MTI. At the conclusion of the AEI (or V-A interval), there having been no P-waves sensed, another A-pulse is generated in order to produce a contraction of the atrium, thereby initiating the next cycle of the heart. Thus, the events previously described begin again and the cycle repeats itself, with a V-pulse being generated after the PVI subsequent to the A-pulse, and an A-pulse being generated after the AEI subsequent to the V-pulse. In this manner, the desired rhythm or synchrony of the heart is maintained as controlled by the programmable PVI and AEI intervals. It is noted that during the refractory periods PVARP and VRP, no cardiac activity can be sensed from the respective heart chambers. Thus, during PVARP, no atrial activity can be sensed. Similarly, during VRP, no ventricular activity can be sensed. (The atrial channel is also refractory during PVI.)

Figure 3B:
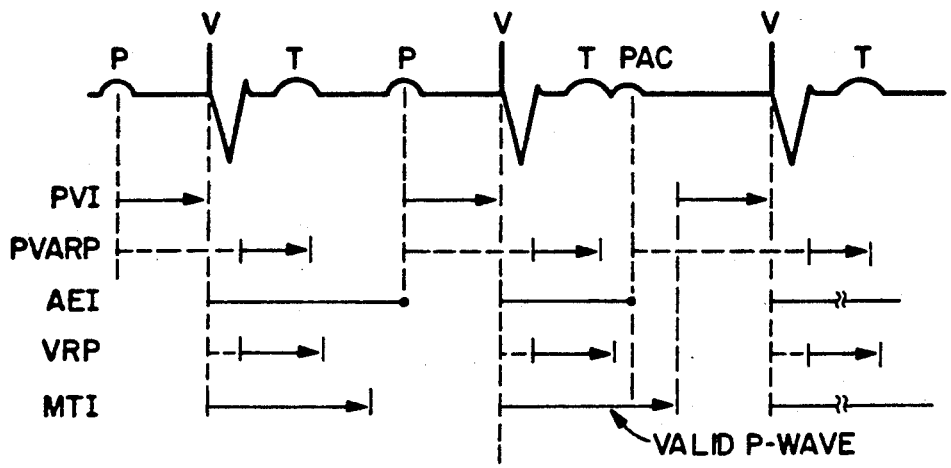
FIG. 3B is a similar composite timing diagram illustrating how AV synchrony is maintained when only a ventricular stimulation pulse need be provided to the heart, and further illustrates one possible response of a pacemaker to a premature atrial contraction (PAC)

In FIG. 3B, a condition is depicted wherein a natural or sinus P-wave is present, and hence there is no need for the pacemaker to generate an A-pulse. When the sinus P-wave is sensed, the P-V interval, PVI, is initiated, and the pacemaker is alert in order to sense if an R-wave will occur. If an R-wave has not been sensed by the time the P-V interval times out, then a V-pulse is generated as indicated. This V-pulse initiates the beginning of the atrial escape interval and PVARP. Prior to the termination of the AEI, a naturally-occurring P-wave is sensed, indicated by the dot on the AEI line. The sensing of the naturally-occurring P-wave inhibits the generation of an A-pulse, and initiates the beginning of a new P-V interval, at the conclusion of which another V-pulse is generated. This process continues for so long as the heart continues to generate sinus P-waves but fails to produce naturally-occurring R-waves.

FIG. 3B further illustrates one possible response of the pacemaker to a premature atrial contraction, or PAC. A premature atrial contraction is simply a contraction of the atrium that occurs prematurely or early in the normal AV synchrony. The PAC shown in FIG. 3B occurs immediately subsequent to the second T-wave. The pacemaker responds to the PAC as though it were a sinus P-wave. That is, the occurrence of the PAC terminates the atrial escape interval. Further, when a P-wave occurs within MTI, as does the PAC shown in FIG. 3B, a latch circuit is set indicating that the sensed activity is considered a valid P-wave. The setting of this latch causes the P-V interval to be initiated at the end of the MTI. At the conclusion of this P-V interval, the V-pulse is generated. Once a V-pulse has been generated, the operation of the pacemaker continues in normal fashion.

Figure 3C:
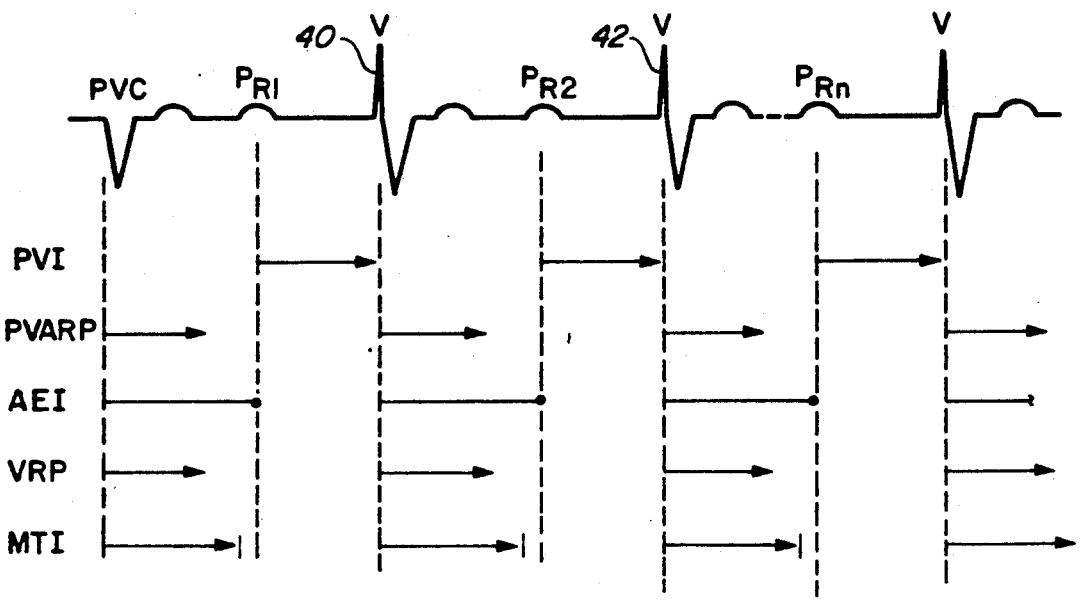
FIG. 3C is a composite timing diagram as in FIGS. 3A and 3B illustrating a PMT at a rate less than the maximum tracking rate (MTR) of the pacemaker.

FIG. 3C is a composite timing diagram as in FIGS. 3A and 3B illustrating a PMT at a rate less than the maximum tracking rate (MTR) of the pacemaker. (The MTR of the pacemaker, as shown in FIG. 3D, is determined by the MTI plus the PVI.) A ventricular contraction, e g., a PVC, triggers a first retrograde P-wave, $P_{R1}$, through retrograde condition as previously described. This retrograde P-wave is interpreted by the pacemaker sensing circuits as a normal P-wave. Thus, its occurrence triggers a P-V interval, PVI. At the conclusion of the PVI, a V-pulse 40 is generated. This V-pulse 40 causes the ventricles to contract, which contraction causes a second retrograde P-wave, $P_{R2}$, to occur. The second retrograde P-wave again triggers a P-V interval, PVI, at the conclusion of which a second V-pulse 42 is generated. The ventricular contraction caused by this second V-pulse 42 causes another retrograde P-wave, and the process repeats.

Note, as seen in FIG. 3C, that the time interval between a ventricular contraction and the occurrence of a retrograde P-wave, $P_R$, is longer than the minimum tracking interval, MTI. Hence, e.g., assuming the minimum tracking interval is 270 msec., and the PVI is 130 msec., the minimum pacing interval (MTI+PVI) is 400 msec., corresponding to a maximum tracking rate (MTR) of approximately 150 bpm (beats per minute). However, because the P-V interval (controlled by the retrograde conduction time) is longer that the MTI, the overall pacing interval, and hence the PMT rate, is greater than 400 msec., resulting in a PMT rate less than the MTR. For example, if the P-V interval is on the order of 310 msec. (some 40 msec. longer than the MTI), then the overall pacing interval is 440 msec., corresponding to a PMT rate of about 136 bpm.

FIG. 3D shows a composite timing diagram illustrating a PMT condition wherein the PMT is constrained to operate at the maximum tracking rate (MTR). In FIG. 3D, it is assumed that this PMT condition is already established. Thus, a V-pulse 44 causes a first retrograde P-wave $P_{R1}$ to occur. This P-wave $P_{R1}$ occurs after the V-pulse 44 at a time that is subsequent to the termination of the PVARP (and hence at a time when the P-wave can be sensed), but is prior to the termination of the MTI. The programmed P-V interval, or PVI, cannot begin until the MTI times out. In this regard, the retrograde P-wave $P_{R1}$ is similar to the PAC shown in FIG. 3B. After the termination of the maximum tracking interval MTI, the programmed P-V interval, PVI, begins, after which another V-pulse 46 is generated A second retrograde P-wave $P_{R2}$ occurs prior to the termination of the next MTI, which MTI is triggered by the V-pulse 46. This process continues, with the retrograde P-wave always occurring prior to the termination of the MTI interval, the PVI not starting until the MTI times out, and the V-pulse being generated at the conclusion of the pacemaker-defined PVI.

Referring next to FIG. 3E, a composite timing diagram illustrates an increasing sinus rate that ends up greater than the pacemaker-defined MTR. The sinus rate is initially sensed by the occurrence of P-waves that occur prior to the termination of the atrial escape interval, AEI, but after the termination of PVARP. The ventricle is stimulated with a V-pulse at the conclusion of the P-V interval (PVI), or programmed P-V delay, which interval or delay is triggered by the occurrence of a P-wave. The interval between the V-pulse and the subsequent P-wave, i.e., the V-P interval, gets progressively shorter until a P-wave 48 falls into PVARP. Once a P-wave falls into PVARP it is not sensed.

It is significant to note for purposes of the present invention that the V-P interval for a sinus rate is not stable. That is, it changes from cycle to cycle, as seen in FIG. 3E. In contrast, for the PMT conditions illustrated in FIGS. 3C and 3D, the V-P interval is more or less stable for each cycle. This is because for the situation where the P-wave is a retrograde P-wave, the entire V-P interval is essentially the retrograde conduction time, which conduction time is more or less constant for a given average cardiac rate. Thus, regardless of whether the PMT is at a rate less than the MTR or equal to the MTR, the V-P interval portion of each PMT cycle is more or less stable, even though other portions of the PMT cycle, e.g., the P-V portion, may momentarily change. This distinction, wherein a PMT includes a stable V-P interval and a non-PMT does not, provides the basis by which the system and method of the present invention is able to recognize whether a fast heart rate condition is a PMT or a non-PMT.

Figure 4A:
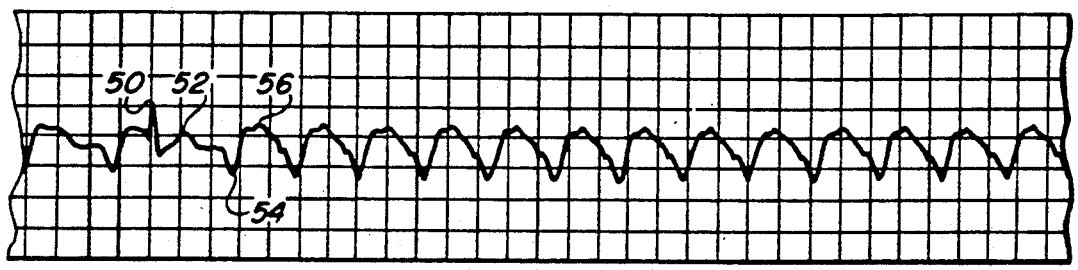
FIGS. 4A, 4B and 4C are actual ECG diagrams corresponding to the conditions shown in FIGS. 3C, 3D and 3E, respectively.
Figure 4B:
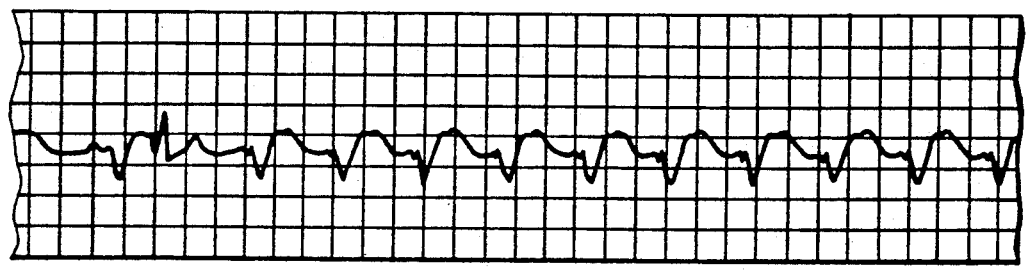
Figure 4C:
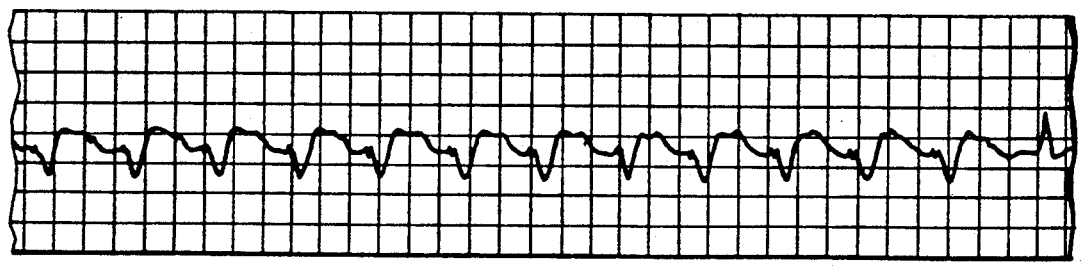

′ FIGS. 4A, 4B and 4C are representations of actual ECG diagrams that correspond, respectively, to the conditions schematically illustrated in FIGS. 3C, 3D and 3E. Each horizontal division in these ECG diagrams corresponds to 200 milliseconds. Each vertical division corresponds to some number of millivolts. In FIG. 4A, the maximum tracking rate is set to 150 beats per minute (bpm). Following a junctional beat 50, e.g. a PVC, there is a T-wave 52 with a retrograde P-wave superimposed thereon. Approximately 130 milliseconds later, the pacemaker paces the ventricle, causing a ventricular contraction, manifest by the inverted R-wave 54. This is followed by yet another retrograde P-wave 56. The PMT continues at approximately 136 bpm (every 440 milliseconds), which is less than the maximum tracking rate.

In FIG. 4B, an ECG representation of a PMT at 110 bpm is shown (545 milliseconds per cycle). The pacemaker is also programmed to have a maximum tracking rate of 110 bpm. Thus, in this case, even though a retrograde P-wave is sensed, the P-V interval (PVI) is not begun because the MTI has not yet timed out. Therefore, when the MTI times out, the PV-interval begins, and a V-pulse is generated upon the timing out of the PVI. Thus, in FIG. 4B, the PMT occurs at the programmed maximum tracking rate of 110 bpm.

In FIG. 4C, the sinus rate manifest by the ECG is faster than the maximum tracking rate. In this case, the V-to-P interval, or "V-P interval", progressively decreases until a P-wave falls into the PVARP and is not sensed. This is not a PMT.

In accordance with the present invention, a system and method for recognizing and terminating a PMT is provided. Broadly stated, this system may be described as a system for detecting the occurrence of a pacemaker mediated tachycardia (PMT) in a patient having an implantable pacemaker. The system includes: (1) first detection means within the pacemaker for detecting a prescribed sequence of cardiac cycles, this prescribed sequence comprising a P-wave followed by a V-pulse at a rate faster than a reference rate, and wherein the time interval between the P-wave and the V-pulse of each cardiac cycle, or the P-to-V interval, comprises a "P-V delay"; (2) means responsive to the first detection means for momentarily changing the P-V delay in a selected cycle; and (3) second detection means for detecting if a V-P interval associated with the selected cardiac cycle remains substantially unchanged from a V-P interval associated with at least one cardiac cycle immediately preceding the selected cardiac cycle.

The V-P interval comprises the time interval between a V-pulse and the occurrence of a P-wave. A substantially unchanged V-P interval associated with the cardiac cycle wherein the P-V delay has been changed (relative to a V-P interval of an adjacent cardiac cycle wherein the P-V delay has not been changed) provides an indication that the prescribed sequence of cardiac cycles comprises a PMT. On the other hand, a V-P interval that is substantially changed provides an indication that the prescribed sequence of cardiac cycles is not a PMT.

Advantageously, the conventional circuits within the pacemaker, e.g., as described above in connection with FIG. 2, or as otherwise known in the art, see, e.g., U.S. Pat. No. 4,712,555, may be used to monitor the cardiac cycle and to determine if the cardiac cycle is of the prescribed type (i.e., a cardiac cycle wherein P-wave tracking occurs as manifest by a P-wave being sensed in each cycle followed by a V-pulse being generated after the programmed PV delay). These same conventional circuits may be used to determine if the rate of the cardiac cycle exceeds a reference rate.

Figure 5:
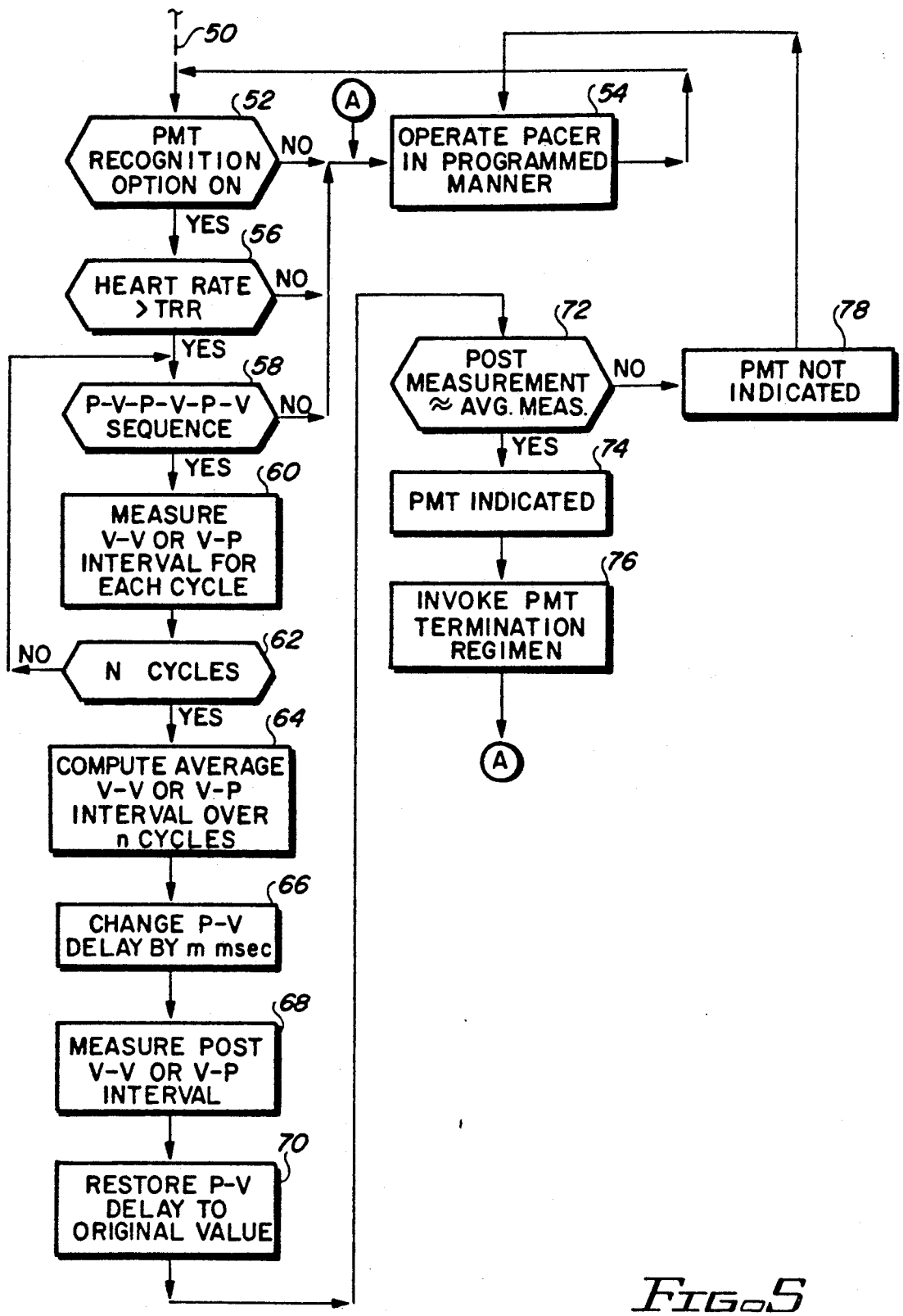
FIG. 5 is a flow chart illustrating one embodiment of the PMT recognition and termination method of the present invention.

Referring to FIG. 5, there is shown a flow chart illustrating the operation of one embodiment of the PMT recognition method of the present invention. In this flow chart, and the other flow charts described herein, the various steps of the PMT recognition method are summarized in individual "blocks" or boxes. Such blocks or boxes describe specific actions or decisions that must be made or carried out as the PMT recognition method proceeds. Specific circuitry that carries out these steps can readily be fashioned by those skilled in the art. Particularly, where a microprocessor, or equivalent programmed-controlled device, is employed as a key element of the pacemaker, i.e., where the control logic 12 (FIG. 2) includes a microprocessor, the flow charts presented herein provide the basis for a "control program" that may be used by such microprocessor, or equivalent, to effectuate the desired control of the pacemaker. Such control program may be stored in ROM (read only memory), RAM (random access memory), or other memory 30 (FIG. 2) associated with the control logic 12. Those skilled in the programming and pacemaker arts may readily write such a control program based on the flow charts and other descriptions presented herein.

As shown in FIG. 5, the flow chart begins with a dashed line 50. This dashed line 50 schematically emphasizes or represents that the program included within the flow chart of FIG. 5 typically forms part of an overall control program associated with the pacemaker.

A first step of the PMT recognition method shown in FIG. 5 involves determining whether the PMT recognition option is turned ON, as depicted in block 52. If not turned ON, then the pacemaker (or "pacer") continues to operate in conventional manner according to its then-existing programmed control parameters, as indicated in block 54. If the PMT recognition option is turned ON, then a determination is made as to whether the heart rate exceeds a reference rate, referred to as the tachycardia reference rate, or TRR (block 56). Any suitable rate determination technique may be used for this purpose. Typically, the heart rate is determined by measuring the interval between succeeding R-waves (whether resulting from a natural or paced contraction). This interval represents the period of the heart rate. (In practice, even though the reciprocal of the heart rate period provides a direct indication of the heart rate, it is the period measurement itself—a time interval measurement—that is used within the pacemaker circuits to provide a measure of the heart rate.) This heart rate interval may be averaged over as many cycles as desired in order to assure that it provides a reliable indicator of the heart rate. For example, an average of the interval or period of the last sixteen cardiac cycles may be computed and compared to the TRR value (which may also be a time interval) to determine if the heart rate is above the TRR threshold value. (Note, that where the TRR value is also a time interval, i.e., a TRR period, a measured heart rate period that is less than the TRR period indicates a heart rate greater than the TRR.)

Continuing with the method shown in FIG. 5, if the heart rate exceeds the TRR value, then a determination is made as to whether the particular sequence associated with a PMT is present, as shown in block 58. For a PMT, this sequence must always include a tracked P-wave followed by a V-pulse for each cardiac cycle. (Stated another way, every V-pulse must be preceded by a P-wave.) Hence, only if the monitored cardiac cycles evidence this P-wave, V-pulse, P-wave, V-pulse, ... sequence, is a PMT possible. If this sequence is not present, then the rapid heart rate condition, determined at block 56, is not a PMT, and the PMT recognition method terminates by returning to operate the pacer in its normal programmed manner (block 54).

If the proper cardiac sequence is detected at block 58, then n cycles of the sequence are monitored in order to measure the V-to-V interval ("V-V" interval), or the V-to-P interval ("V-P" interval) of each cycle, as indicated at blocks 60 and 62 of the flow chart. If at any time during the monitoring of these n cycles, the proper sequence does not continue, the method terminates. The number of cardiac cycles thus monitored, i.e., the value of n for this embodiment of the invention, is preferably about 10 cardiac cycles. However, it may be any value, e.g., two to twenty, which value may be programmably set to a desired value.

After n cycles of the P-V-P-V- . . . sequence are monitored, where n is a selected integer, the average V-V interval (or V-P interval) is computed for the n cycles (block 64). Then, the P-V delay of the pacemaker is changed by a prescribed amount, indicated in block 66 as "m milliseconds". The P-V delay is a programmable parameter associated with the operation of the pacemaker, and represents the pacemaker induced delay after a P wave is sensed before which a V-pulse is generated. (Of course, the sensing of an intrinsic or natural R-wave during the P-V delay inhibits the generation of the V-pulse for many pacemaker modes.) The preferred amount by which the P-V delay is changed, in accordance with one embodiment of the invention, is to shorten the P-V delay by about 50 milliseconds. It is to be understood, however, that the P-V delay could be changed by any desired value.

After the P-V delay has been changed, the V-V interval (or V-P interval) of the next cardiac cycle is measured (block 68), providing a "post measurement" of this value. Once this post measurement has been made, the P-V delay is restored to its original value (block 70). A comparison is then made between the post measured value of the V-V interval (or V-P interval), where this post measured value is the V-V (or V-P) interval that occurs immediately after the changed P-V delay, with the average V-V interval (or V-P interval) previously computed (block 72). If this comparison indicates that the V-V interval (or V-P interval) is substantially unchanged, e.g., that the two values are within about 25 milliseconds of each other, then a PMT is indicated (block 74). Accordingly, an appropriate PMT termination regimen, such as extending PVARP, is invoked for one or more cardiac cycles (block 76). After invoking the PMT termination regimen, the pacemaker continues to operate in its programmed manner (block 54). If the PMT continues, i.e., if the PMT termination regimen was not successful in terminating the PMT, then the PMT recognition process repeats.

If, on the other hand, the comparison performed at block 72 indicates that the V-V interval (or V-P interval) is substantially changed, then a PMT is not indicated (block 78), and the pacer continues to operate in its programmed manner (block 54).

Figure 6:
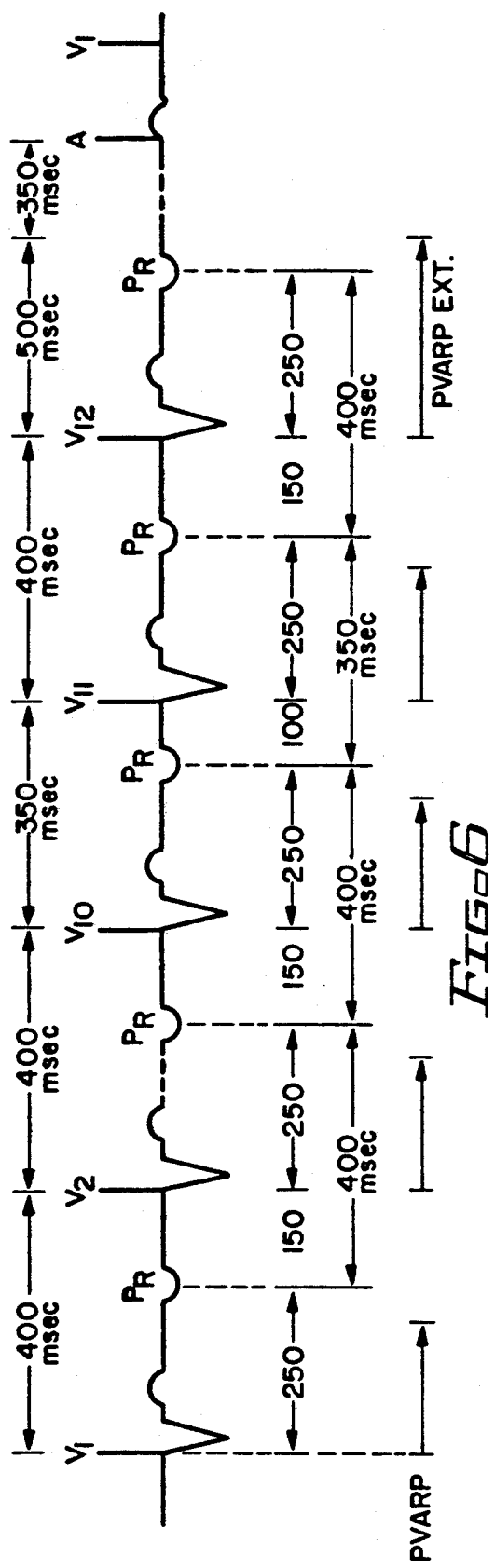
FIG. 6 is a composite timing diagram showing the termination of a PMT in accordance with the method shown in FIG. 5.
Figure 7:
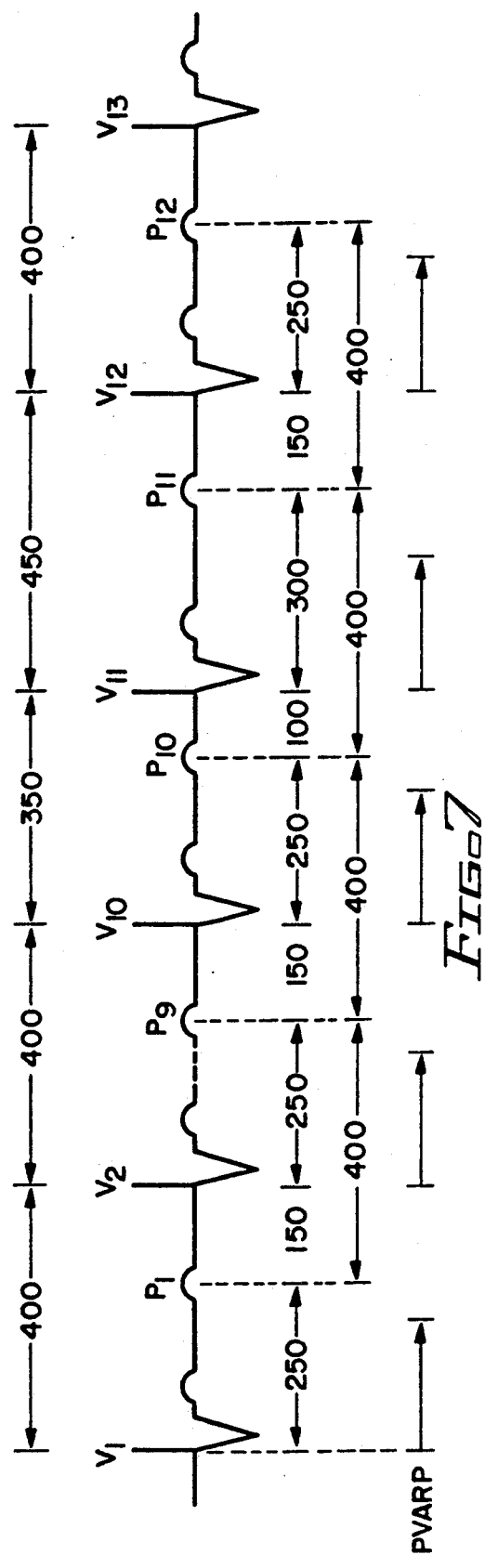
FIG. 7 is a composite timing diagram illustrating how the method of FIG. 5 properly recognizes a sinus drive as a non-PMT condition.

Operation of the PMT recognition method shown in FIG. 5 is illustrated by the composite timing diagrams of FIGS. 6 and 7. FIG. 6 illustrates a PMT condition, and FIG. 7 illustrates a non-PMT condition. In both FIGS. 6 and 7 it is assumed that a fast tachycardia condition exists containing the proper sequence of P-waves and V-pulses. That is, the tests imposed by both blocks 56 and 58 of the flow chart of FIG. 5 have been passed.

In FIG. 6, a first V-pulse, $V_1$, and a second V-pulse, $V_2$, are separated by 400 msec., which time is less than the programmed maximum tracking interval. The cardiac cycle measured between $V_1$ and $V_2$ is comprised of a V-to-P interval of 250 milliseconds (msec), and a P-to-V interval of 150 msec. The P-to-V interval is set by the programmed PV delay of the pacemaker. Additional V-pulses, not shown, up to a tenth V-pulse, $V_{10}$, are similarly separated by approximately 400 msec., making a total of nine (9) cardiac cycles (measured from V-pulse to V-pulse) that have occurred sequentially, each containing the requisite P-wave and V-pulse. During each cycle, the V-P interval is measured. The average V-P interval is then computed over the nine cardiac cycles to be 250 msec.

In accordance with the embodiment of the invention shown in FIG. 5, after the prescribed number of cardiac cycles meeting the specified criteria have occurred, e.g., nine cardiac cycles each having a V-to-V interval less than the reference interval, with each interval containing a P-wave followed by a V-pulse, the P-V delay of the next cardiac cycle is shortened by a prescribed amount, e.g., 50 msec. Thus, in FIG. 6, after the 10th V-pulse, $V_{10}$, the P-V delay of the next cardiac cycle is shortened by 50 msec. This causes the next P-V interval to be equal to 100 msec., which action also shortens the total V-V interval between $V_{10}$ and $V_{11}$ to 350 msec. because the V-P interval (which in this instance is essentially the retrograde conduction time) remains approximately the same. After shortening the P-V delay for one cycle, it is restored to its original value of 150 msec. Thus, during the next V-V interval, between $V_{11}$ and $V_{12}$, the P-V portion is restored to 150 msec., and the total V-V interval time returns to 400 msec. Because the V-P interval subsequent to shortening the P-V delay remains substantially unchanged from the V-P intervals prior to shortening the P-V delay, e.g., at 250 msec., a PMT is indicated. Thus, an appropriate PMT termination regimen is invoked. In this case, this regimen involves extending the PVARP interval of the next cycle, beginning with the cycle that starts with V-pulse $V_{12}$. This extension prevents the next retrograde P-wave from being sensed, thereby breaking the PMT. Note that during this process, the PMT termination regimen is invoked for only one cycle. It is noted that in this instance, shortening the P-V interval by 50 msec. (or another appropriate amount) may, by itself, extinguish the PMT. However, if it does not, lengthening the next PVARP should extinguish the PMT. It is thus seen that the present invention quickly terminates a PMT, once a PMT is detected, and that the PMT response used to terminate the PMT lasts for only a short time, e.g., one cardiac cycle.

In FIG. 7, a non-PMT condition is illustrated. As with FIG. 6, it is assumed that a prescribed number of cardiac cycles has occurred, each having a P-wave followed by a V-pulse, and each having a V-V interval less than the prescribed reference TRR. Hence, in accordance with this embodiment of the invention, the P-V delay is shortened by 50 msec. Thus, during the next V-V interval, between $V_{10}$ and $V_{11}$, the P-V delay is shortened to 100 msec. However, this action causes the next V-P interval, between $V_{11}$ and $P_{11}$, to also change. In this case, the amount of change is shown as an additional 50 msec., although this increase is only exemplary. In any event, because the V-P interval is not a retrograde conduction, but a component of sinus rate, the V-P interval following the shortened P-V delay is substantially different than the average V-P intervals measured during the previous cardiac cycles, e.g., from $V_1$ through $V_{10}$. Hence, the method of FIG. 5 operates to find the tachycardia condition represented in FIG. 7 as not being a PMT, but rather a sinus drive condition. Accordingly, a PMT termination regimen is not necessary nor desired.

Figure 8:
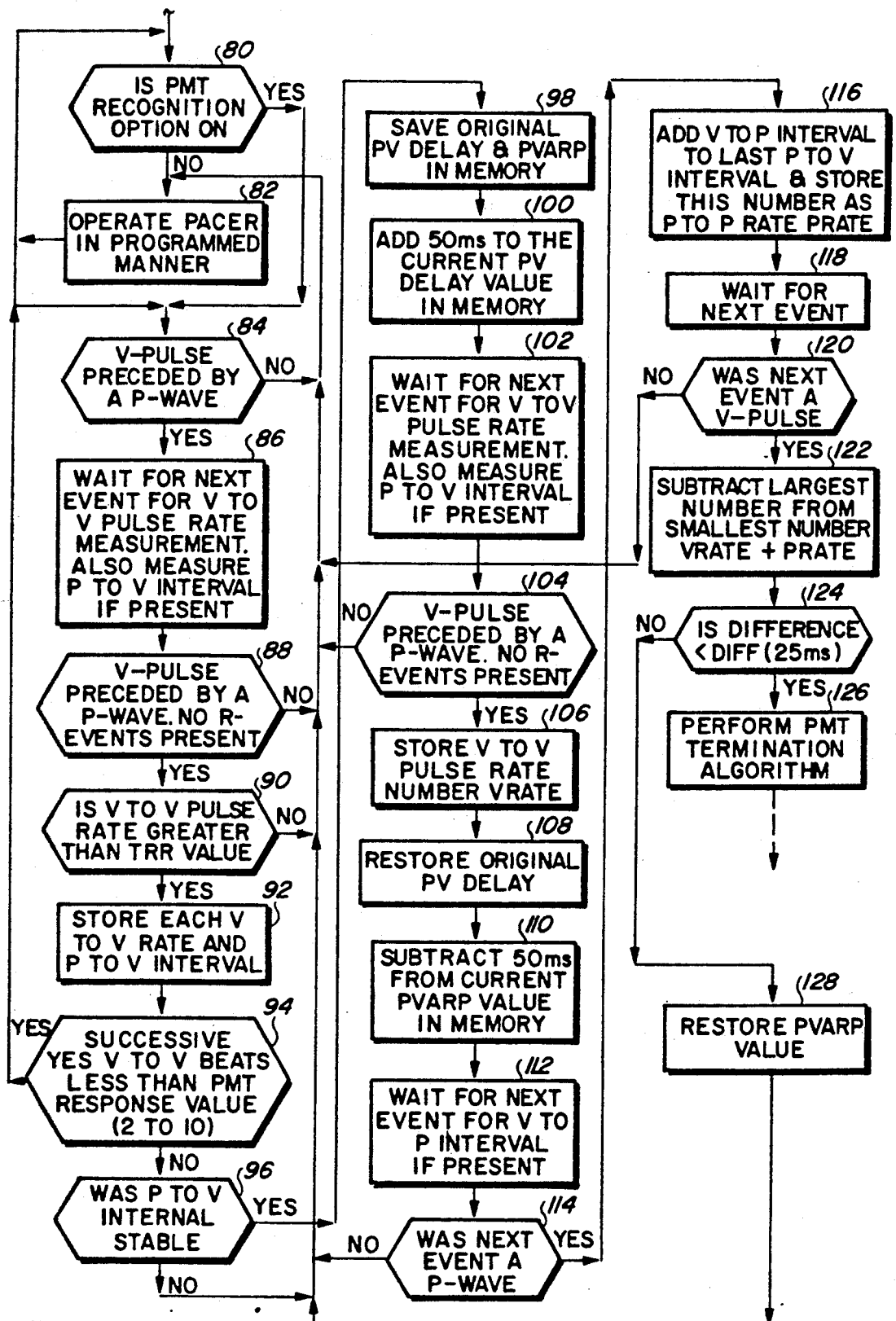
FIG. 8 is a flow chart illustrating another embodiment of the PMT recognition and termination method of the present invention.

Referring next to FIG. 8, a flow chart illustrating the operation of another embodiment of the PMT recognition and termination system and method of the present invention is shown. The system and method shown in FIG. 8 is generally preferred over that shown in FIG. 5 because it is easier to implement and can work at any P-wave rate, including rates at or above maximum tracking rate. This is not to suggest, however, that the system described in connection with FIG. 5 should not be used. To the contrary, there are many applications where the technique shown in FIG. 5, or techniques equivalent thereto (e.g., involving a momentary shortening of the P-V delay), may be most beneficial.

In general, the method shown in FIG. 8 may be characterized as a method for detecting a PMT that includes the steps of:

(a) sensing a P-wave followed by a V-pulse in a plurality of successive cardiac cycles;

(b) sensing if the plurality of successive cardiac cycles sensed in step (a) occurs at a rate in excess of a tachycardia reference rate (TRR);

(c) increasing a P-V delay in a single cardiac cycle when the rate of the plurality of successive cardiac cycles sensed in step (b) exceeds the TRR;

(d) measuring a V-V time interval associated with the single cardiac cycle of step (c), this V-V time interval comprising the elapsed time between a first V-pulse and a second V-pulse, a first P-wave occurring after the first V-pulse and prior to the second V-pulse, and the increased P-V delay of step (c) being included in the V-V time interval as the time interval between the first P-wave and the second V-pulse;

(e) measuring a P-P time interval associated with the single cardiac cycle of step (c), this P-P time interval comprising the elapsed time between a first P-wave and a second P-wave, the second P-wave occurring after the second V-pulse, and the increased P-V delay of step (c) being included in the P-P time interval as the time interval between the first P-wave and the second V-pulse;

(f) measuring the difference between the V-V time interval and the P-P time interval; and (g) indicating a PMT condition when the difference between the V-V time interval and the P-P time interval is less than a prescribed difference.

As seen in FIG. 8, the method shown, like the method shown in FIG. 5, is intended to form part of an overall control program of the pacemaker. As such, the method may be selected through conventional programming techniques to be turned ON or turned OFF. Thus, as a first step (block 80), a determination is made as to whether the PMT recognition feature is turned ON. If not (block 82), then the pacer continues to operate in its conventional programmed manner. If the PMT recognition feature is turned on, a determination is made (block 84) as to whether there is a V-pulse preceded by a P-wave. If not, the PMT recognition method is aborted and the pacer reverts to operating in its normal programmed mode (block 82). If there is a V-pulse preceded by a P-wave, then there is a pause to wait for the next ventricular event so that a V-V pulse rate measurement (which is really a V-V time interval measurement as discussed above) may be made (block 86). Further, the P-V interval within the V-V interval may be measured.

Next, a determination is again made as to whether there is a V-pulse preceded by a P-wave, and that no R-waves are present (block 88). If so, a determination is made as to whether the V-V interval pulse rate is greater than a tachycardia reference rate (TRR) value (block 90). Again, as with FIG. 5, this determination is best made by comparing time intervals, not time rates. If either of these tests fail, that is, if there is not a V-pulse preceded by a P-wave, or if there is an R-wave present (evidencing natural, non-paced, ventricular activity), or if the V-V interval is greater than the TRR interval, then the PMT recognition system is aborted and the pacer returns to operating in its normal programmed manner (block 82).

If the V-V interval (determined at block 90) is less than the TRR interval (i.e., if the V-V rate is greater than TRR), then each V-V rate interval and each P-V interval is stored (block 92). Then, a determination is made (at block 94) as to how many V-V intervals have been monitored in this fashion. If the number of intervals is less than a programmed number, which programmed number will typically be between two and ten, then the method reverts to block 86 so that the process (carried out in blocks 86, 88, 90, 92 and 94) can be repeated for each V-V interval.

Once the number of V-V intervals equals the programmed number, a determination is made (at block 96) as to whether the P-V interval is stable. Stability is determined by comparing the P-V intervals stored (in block 92) for each of the programmed number of V-V intervals to ascertain how much the stored P-V intervals vary. For example, if each stored P-V interval is within a prescribed variance, e.g., 25 msec., of the other stored P-V intervals, then P-V stability is established. If P-V stability is not established, the PMT recognition method is aborted, and the pacer returns to operating in its normal programmed manner (block 82). If P-V stability is established, then the original P-V delay is stored in memory along with PVARP (block 98). These "original" P-V delay and PVARP settings will be restored after changing these parameters during the PMT test. Next, a programmed increase, e.g., 50 msec., is added to the current PV delay value stored in memory (block 100). Then, the system waits for the next event so that a V-V interval measurement (V-V pulse rate measurement) may be made. The V-V interval containing this lengthened P-V delay is referred to as a lengthened V-V interval. Further, the P-V interval that forms part of this lengthened V-V interval is also measured (block 102).

After the lengthened V-V interval has occurred, another determination is made (at block 104) as to whether there is a V-pulse preceded by a P-wave. If not, the PMT has been terminated simply by lengthening the P-V delay, and the PMT recognition routine may be terminated (by returning to block 82 and having the pacer operate in its normal programmed manner). A determination that an R-wave is present also provides an indication that the PMT has been terminated (also included in the test of block 104) and that the PMT recognition method may be terminated. Upon returning to the normal programmed operation of the pacer (block 82), the original P-V delay is restored.

If, however, there is no R-wave, but rather there is a V-pulse preceded by a P-wave (as determined at block 104), then further evaluation must continue to determine whether a PMT is present. This is done by first storing the V-V interval most recently measured (at block 102) as a parameter termed VRATE (block 106). Then, the original PV delay is restored (block 108), and PVARP is decreased by the programmed increase of the PV delay, e.g., PVARP is decreased by 50 msec. (block 110). This is done to maintain tracking of P-waves if this is a non-PMT, i.e. sinus, rate. Then, the method waits for the next event, e.g. P-wave, so that a V-P interval may be measured (block 112). If this next event is not a P-wave (determined at block 114), then the PMT recognition technique is aborted. If however, the next event is a P-wave, then the V-P interval is added to the last P-V interval, with the result being stored as a P-P interval, termed PRATE (block 116).

After PRATE has been determined, it is necessary to wait for the next event (block 118). If the next event is not a V-pulse, determined at block 120, then the PMT recognition routine is aborted (i.e., control returns to block 82). If the next event is a V-pulse, then VRATE and PRATE are compared (blocks 122 and 124). Typically, this is accomplished by subtracting the smallest of the two values from the largest (block 122), and then comparing the difference to a reference value, DIFF (block 124). The DIFF reference value may be any desired programmed value. In a preferred embodiment it is about 25 msec.

If the comparison of the PRATE and VRATE values indicates that they are substantially the same, e.g., within 25 msec. of each other, then that provides an indication that a PMT is present. Accordingly, a desired PMT termination routine is invoked (block 126). If PRATE and VRATE are not substantially the same, then that provides an indication that a PMT is not present. Accordingly, the PVARP value is restored (block 128) and the pacer returns (to block 82) to operate in its normal programmed manner.

As thus described, it is seen that the PMT recognition method operates as part of the overall pacemaker control program and does not interfere with such operation. Rather, it advantageously interleaves with the pacer's operation in a way that is essentially transparent to the pacer's normal programmed operation. Thus, the method may be implemented equally effectively in a rate-responsive pacer or in a fixed (programmable) rate pacer.

Any suitable PMT termination routine may be invoked once a PMT is determined to be present (as determined, e.g., by carrying out the process shown in FIG. 5 or FIG. 8). A preferred PMT termination routine is as follows: Upon the first determination or recognition that a PMT is present, PVARP is extended for one cycle. Thus, unlike the prior art technique described above, if a ventricular beat (an R-wave or a PVC) is sensed before a sensed P-wave or a delivered A-pulse, the system will not continue to extend PVARP. After extending PVARP for one cycle, the pacer continues to operate in its programmed manner. This programmed manner includes the PMT recognition process described above, and will terminate a PMT.

Optionally, upon completing the PMT termination process for a first time, if an R-wave is sensed without first sensing an atrial event, the PVARP will be extended one time, e.g., one cardiac cycle. Thus, if this option is selected, upon the second extension of PVARP, the termination cycle is completed. In this manner, it is thus not possible for a PMT termination routine to become "stuck" for a prolonged period of time, as could happen with prior art termination routines. Thus, the overall heart rate is never forced lower than it should be for any sustained period of time.

Figure 9:
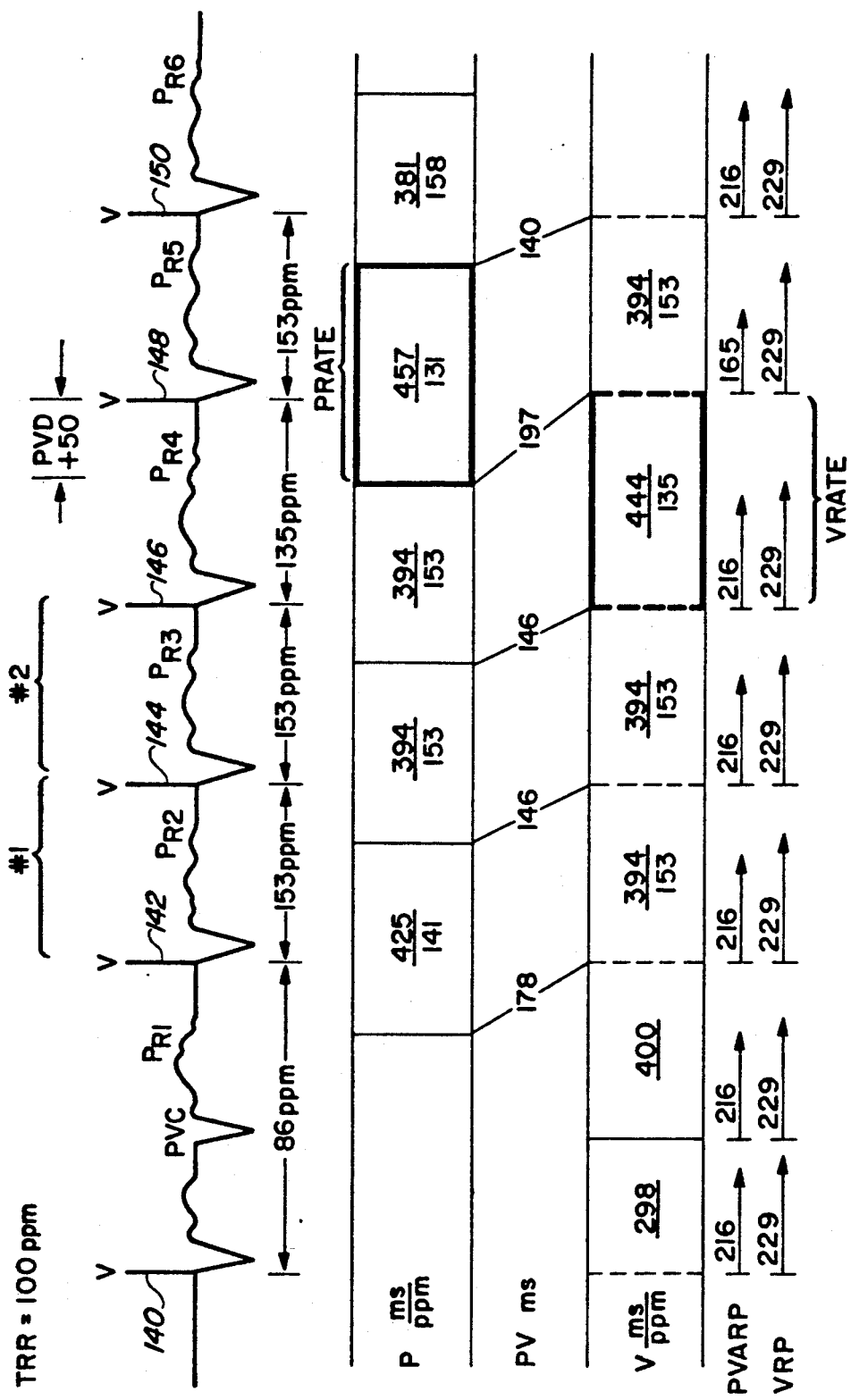
FIG. 9 is a composite timing diagram showing operation of the method depicted in FIG. 8 to recognize a PMT.

Referring next to FIG. 9, a composite timing diagram showing operation of the method depicted in FIG. 8 to recognize a PMT is shown. In FIG. 9, it is assumed that TRR is set to 100 bpm (meaning the TRR interval or period is set to 600 msec.), and that the programmed number of V-V cycles that must occur with a rate greater than TRR is two. Values for both beats per minute, or pulses per minute (ppm) and corresponding time periods (expressed in milliseconds, or "msec.") are included for each cycle shown in FIG. 9. At the top of FIG. 9 is a representation of the ECG waveform, starting with a V-pulse 140. After the V-pulse 140, a PVC occurs, which PVC triggers a retrograde P-wave, $P_{R1}$. One P-V delay after the retrograde P-wave, which P-V delay is 178 msec., another V-pulse 142 is generated. The time interval between the V-pulse 140 and the V-pulse 142 is 698 msec., corresponding to a rate of 86 ppm. This is less than the TRR value of 100 ppm. However, after the V-pulse 142, a second retrograde P-wave $P_{R2}$ occurs. This in turn causes another V-pulse 144 to be generated one P-V delay later. In this case the P-V delay between $P_{R2}$ and the V-pulse 144 is 146 msec. (Note, that the actual measured P-V delay will not always be equal to the programmed P-V delay due to the response time of the cardiac tissue to a stimulation pulse. This response time varies depending upon the state of the tissue at the time it is stimulated.) The time interval between the V-pulse 142 and the V-pulse 144 is 394 msec., corresponding to a rate of 153 ppm. This rate is greater than the TRR value. Hence, this represents the first V-V cycle, labeled "#1" in FIG. 9, having a length (period) corresponding to a rate greater than TRR.

Following the #1 V-V cycle, a nearly identical V-V cycle follows, labeled "#2" in FIG. 9. This #2 V-V cycle begins with V-pulse 144 and terminates with another V-pulse 146. This #2 cycle has a rate of 153 ppm, a P-V interval of 146 msec., and a V-V interval of 394 msec. Both the #1 and #2 V-V cycles include a PVARP interval of 216 msec. and a VRP interval of 229 msec. as shown at the bottom of FIG. 9.

At the conclusion of the #2 V-V interval, i.e., after the V-pulse 146, the programmed P-V delay (PVD) is increased by 50 msec. This causes the next V-V interval, beginning with the V-pulse 146 and concluding with a V-pulse 148, to also increase or lengthen by roughly 50 msec. Thus, this next V-V interval, labeled "VRATE" in FIG. 9, has a total interval length of 444 msec., corresponding to a rate of 135 ppm. The VRATE interval includes the lengthened P-V delay.

The P-wave that occurs during the VRATE interval, identified as $P_{R4}$, begins a P-P cycle commencing with P-wave $P_{R4}$ and concluding with a P-wave $P_{R5}$. This P-P cycle overlaps the VRATE cycle and is identified in FIG. 9 as PRATE. This PRATE cycle also includes the lengthened P-V delay. The interval of the PRATE cycle is 457 msec., corresponding to a rate of approximately 131 ppm.

The P-V delay is lengthened for only one cycle, i.e., between $P_{R4}$ and the V-pulse 148. After that, it is returned to its prior value. Thus, the V-V cycle that follows the VRATE cycle, which starts with V-pulse 148 and terminates with a V-pulse 150, does not include the lengthened P-V delay. Accordingly, the V-V interval of this cycle returns to about 394 msec. Similarly, the P-P cycle that follows the PRATE cycle, which begins with P-wave P_{R5} and concludes with P-wave P_{R6}, does not include the lengthened P-V delay, and has an interval time of 381 msec.

In accordance with the process summarized in FIG. 8, whether or not a PMT is present is determined by comparing the value of the VRATE interval to the value of the PRATE interval. This comparison, for the situation shown in FIG. 9, yields a difference of 13 msec. Assuming a programmed DIFF value of 25 msec., it is seen that this 13 msec. difference is less than the DIFF value, and hence a PMT is indicated.

Figure 10A:
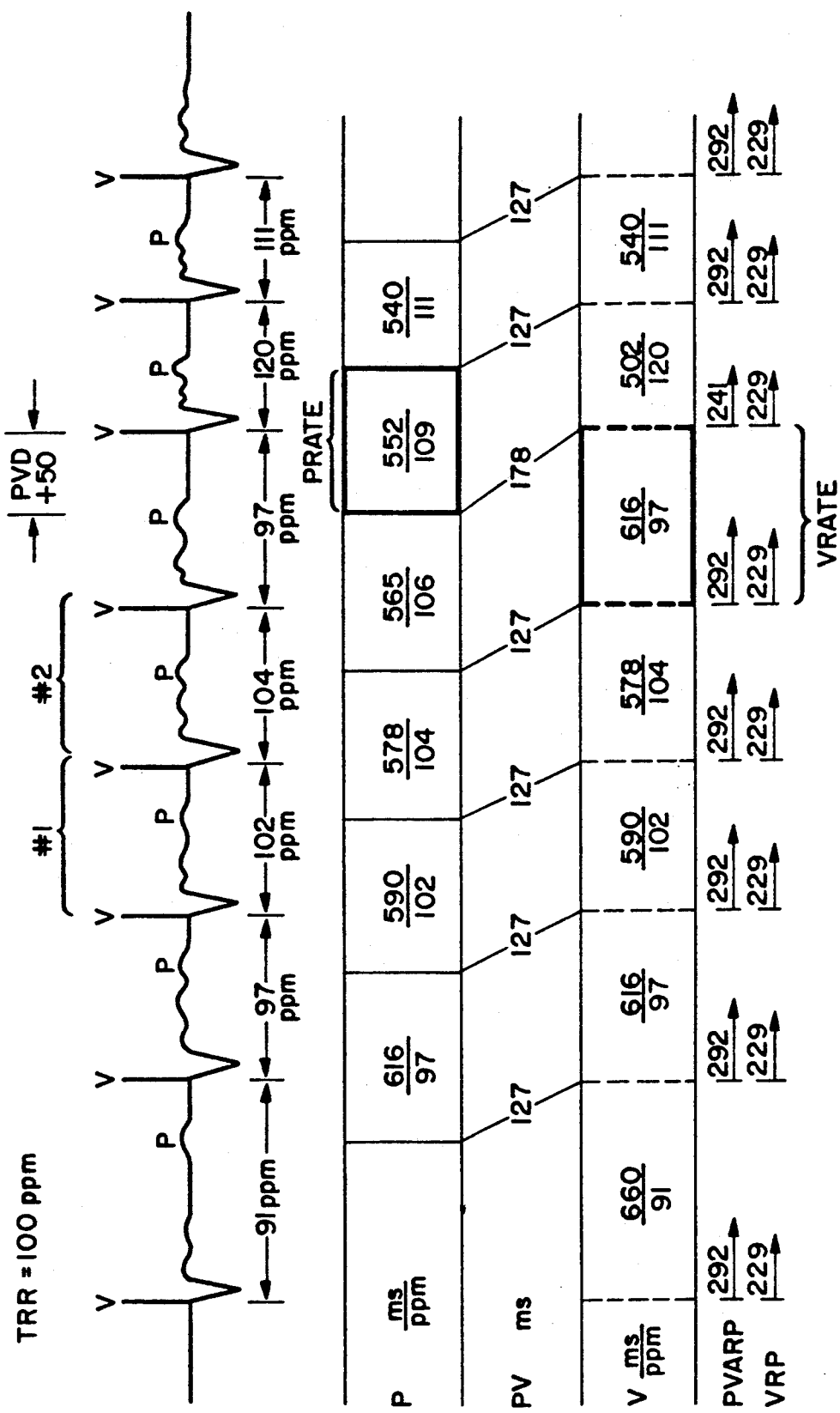
FIG. 10A is a composite timing diagram showing a sinus tachycardia having an increasing rate, and illustrates the operation of the method of FIG. 8 to recognize this condition as a non-PMT.
Figure 10B:
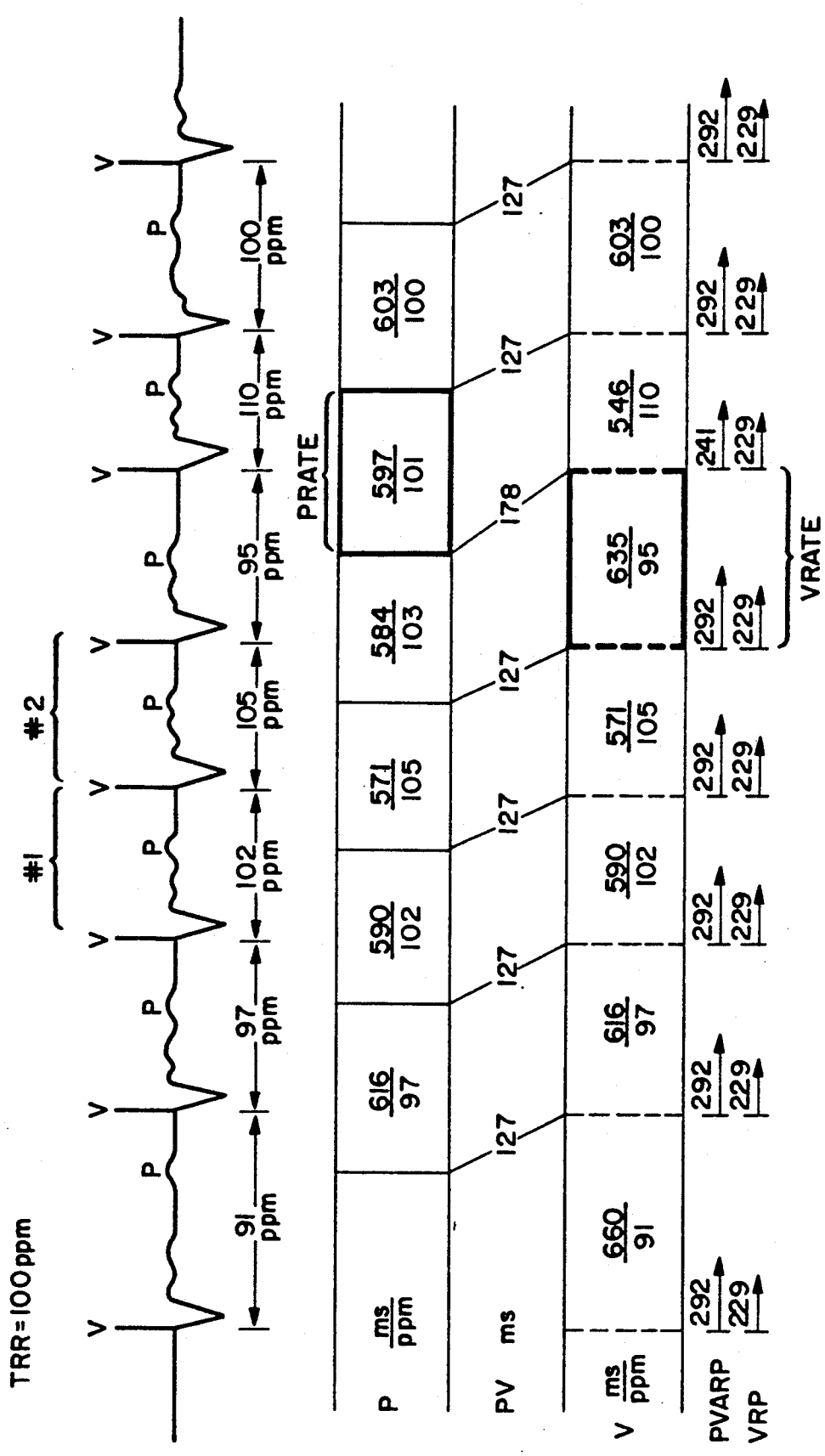
FIG. 10B is a composite timing diagram showing a sinus tachycardia having a decreasing rate, and illustrates the operation of the method of FIG. 8 to recognize this condition as a non-PMT.
Figure 10C:
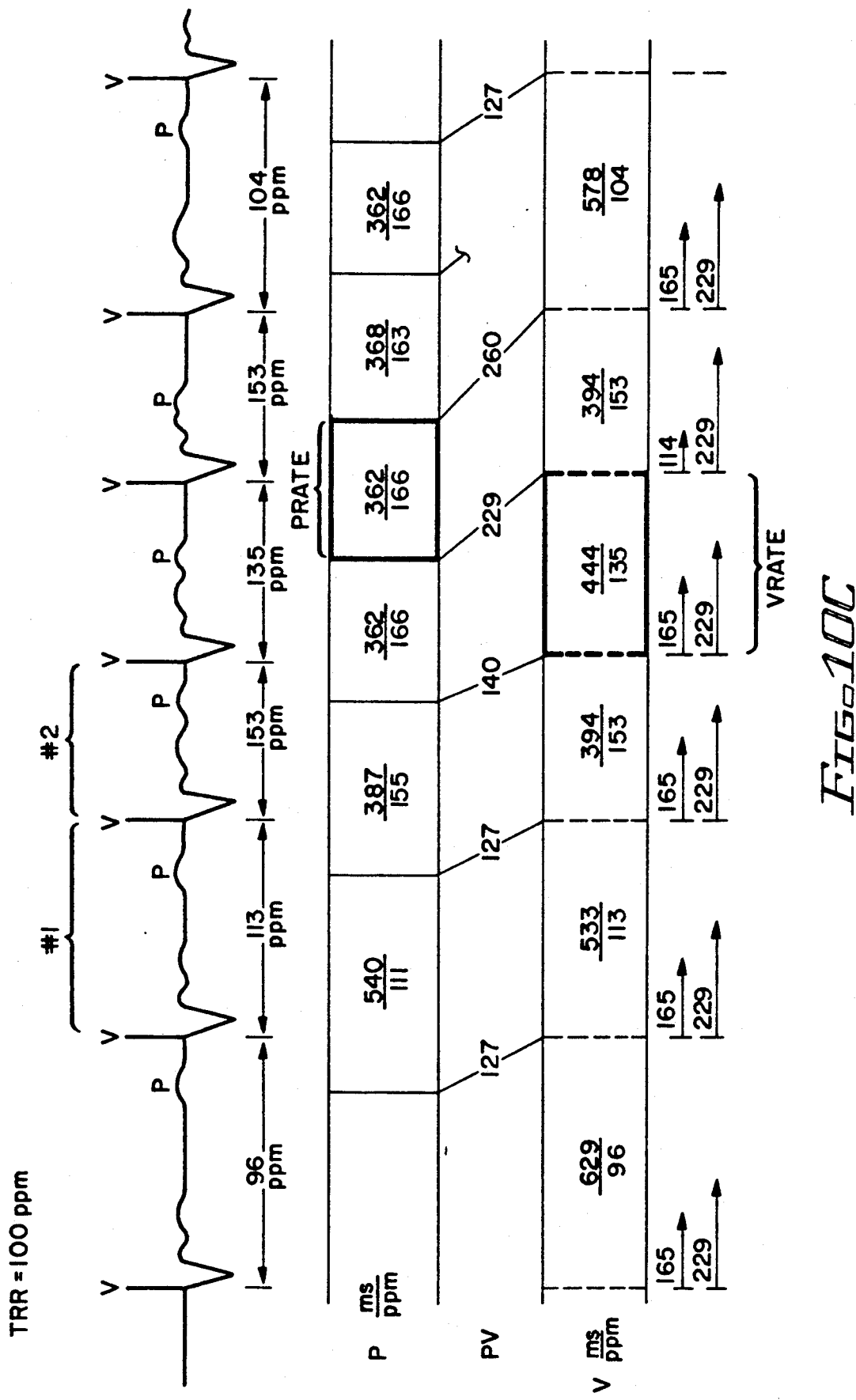
FIG. 10C is a composite timing diagram showing a paroxysmal atrial tachycardia, and further illustrates the operation of the method of FIG. 8 to recognize this condition as a non-PMT.

FIGS. 10A, 10B and 10C are composite timing diagrams similar to FIG. 9 showing various sinus tachycardia conditions wherein the process of FIG. 8 is used to determine that a PMT condition does not exist. In FIG. 10A, for example, a progressively increasing sinus rate is present. After two consecutive cycles having an effective rate in excess of the TRR are detected, labeled #1 and #2, the P-V delay of the next V-V cycle, labeled VRATE, is increased. This cycle has a value of 616 msec. The overlapping P-P cycle that also includes the lengthened P-V delay, labeled PRATE, has a length of 552 msec. The difference between 616 msec. and 552 msec. is greater than 25 msec., the DIFF reference value. Hence, the condition shown in FIG. 10A is not a PMT.

In FIG. 10B, another non-PMT condition is illustrated. In this instance, two consecutive V-V cycles, #1 and #2, have intervals less than the TRR interval. (Said another way, the V-V cycles labeled #1 and #2 have an effective rate in excess of the TRR.) Following these two V-V cycles, the P-V delay of the next cycle is increased the prescribed amount, e.g., 50 msec. As with FIGS. 9 and 10A, the next V-V cycle containing this lengthened P-V delay is labeled VRATE, and the next overlapping P-P cycle containing this lengthened P-V delay is labeled PRATE. The duration of the VRATE cycle is 635 msec. The duration of the PRATE cycle is 597 msec. The difference between VRATE and PRATE is 38 msec. This difference is greater than the reference difference DIFF, so again a PMT is not indicated.

Similarly, in FIG. 10C, a paroxysmal atrial tachycardia condition is shown which is not a PMT. Following the procedure outlined above in connection with FIG. 8, a VRATE cycle having an interval or period of 444 msec. is generated by lengthening the P-V delay after the occurrence of two consecutive V-V cycles having an effective rate greater than the TRR. Likewise, a PRATE cycle, also containing the lengthened P-V delay, and having an interval of 362 msec. is generated. The difference between the PRATE and VRATE interval values is 82 msec. Hence, this tachycardia condition is not a PMT.

Figure 11:
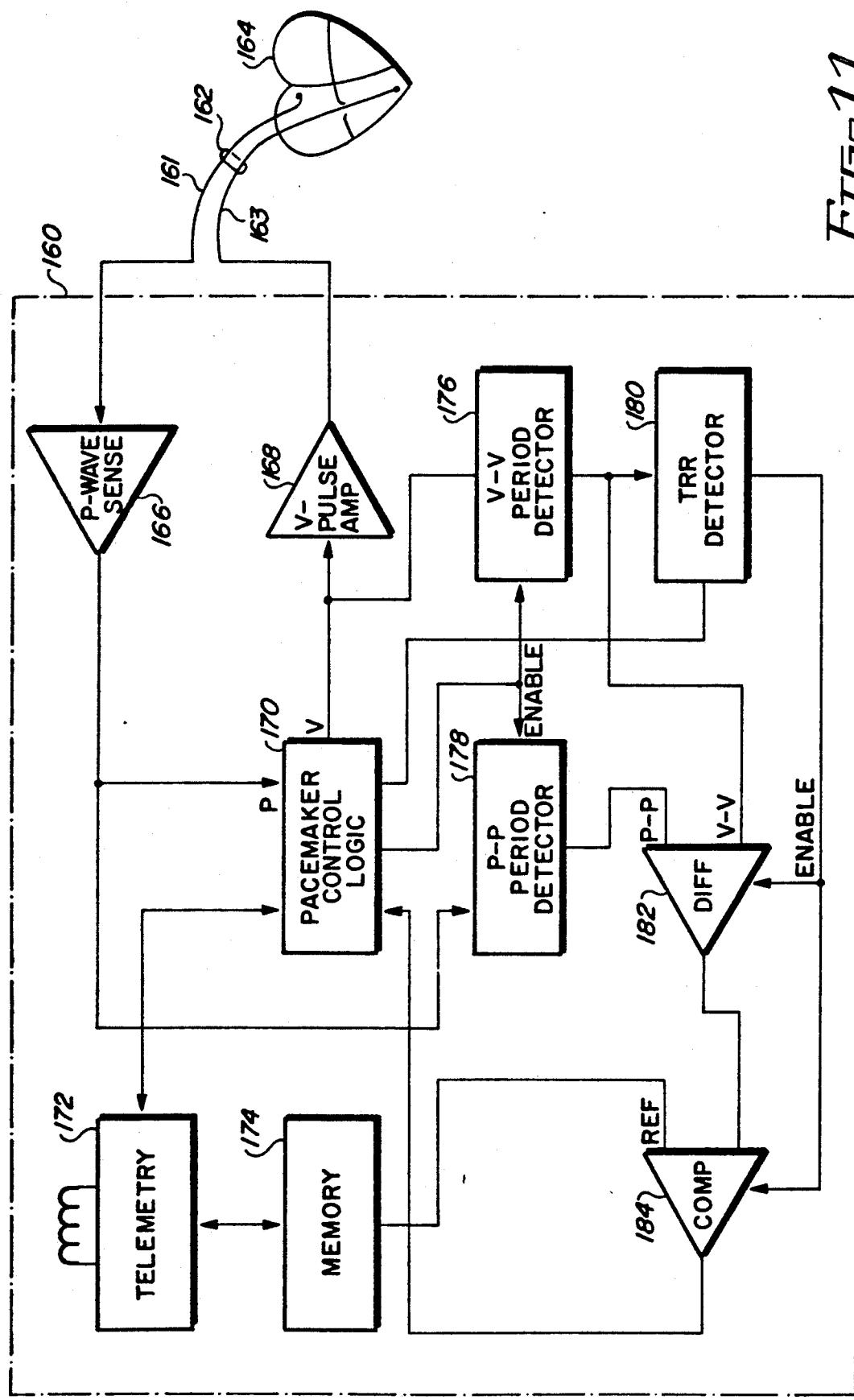
FIG. 11 is a block diagram of one type of apparatus that may be used in carrying out the method depicted in FIG. 8.

Referring next to FIG. 11, a functional block diagram of one type of apparatus that may be used in carrying out the method depicted in FIG. 8 is shown. As seen in FIG. 11, a pacemaker 160 interfaces with a mammalian heart 164 by way of a pacemaker lead 162. The pacemaker lead 162 includes an atrial conductor 161 for making electrical contact with the right atrium of the heart 164 and a ventricular conductor 163 for making electrical contact with the right ventricle of the heart. The atrial conductor 161 is connected to a P-wave sense amplifier 166 included within the pacemaker 160. Similarly, the ventricular conductor 163 is connected to a V-pulse amplifier 168, also included within the pacemaker 160. (Not shown in FIG. because such are not needed to carry out the invention, but typically included within the pacemaker 160, are an atrial A-pulse amplifier and a ventricular sense amplifier, as shown in FIG. 2.)

The pacemaker 170 further includes pacemaker control logic 170 coupled to a memory 174 and telemetry circuits 172. The operation of the control logic 170, P-wave sense amplifier 166, V-Pulse amplifier 168, memory 174 and telemetry circuits 172 in tracking P-waves and stimulating the ventricles is conventional. Upon sensing a P-wave, the output of the P-wave sense amplifier generates a P signal. This P signal is directed to the control logic 170 and to a P-P period detector 178. Similarly, the generation of a V-pulse is triggered whenever the control logic 170 generates a V signal and directs it to the input of the V-pulse amplifier 168. This V signal is also coupled to a V-V period detector 176. The P-P period detector 178 measures the time interval between P signals, i.e., between sensed P-waves. The V-V period detector 176 measures the time interval between V-pulses. Both the P-P period detector 178 and the V-V period detector 176 are enabled by the control logic 170. The logic circuits within the control logic 170 are configured to enable these circuits only when the proper sequence of cardiac signals occurs, i.e., only when there are V-pulses preceded by P-waves.

It is noted that the programmed values of TRR, the number of cardiac cycles n (two to ten) that must be greater than TRR in order to trigger the lengthening of the P-V delay, the PVARP value, the DIFF reference value, and other values associated with operation of the PMT recognition process are programmably stored in the memory 174 in conventional manner.

A TRR detector 180 determines if the V-V intervals determined by the V-V period detector are less than the TRR interval. If so, an output signal from the TRR detector 180 enables a difference amplifier 182 and a comparator circuit 184. The difference amplifier 182 determines the difference between the P-P period and the V-V period. This difference is compared with a reference DIFF value, obtained from the memory 174, in the comparator circuit 184. This difference is then directed back to the control logic 170 where it is used to determine if a PMT condition exists if the other conditions are present, i.e., if the programmed number of consecutive V-V intervals are present having a rate in excess of the TRR, and if the P-V delay has been extended. It is noted that the logic circuits for momentarily extending the P-V delay and shortening PVARP are included within the control logic circuits 170.

Those skilled in the art will readily recognize that many of the functions referenced in FIG. 11 may be carried out within the control logic 170 using the already existing control logic circuits. In fact, where the control logic circuits 170 comprise a microprocessor circuit, or equivalent, all of the functions performed by the P-P period detector 178, the V-V period detector 176, the TRR detector 180, the difference amplifier 182, and the comparator 184 may be carried out by the microprocessor.

As described above, it is thus seen that the present invention provides a system or method for accurately detecting the occurrence of a PMT, and for quickly terminating the PMT once detected. The disclosed system and/or method reliably detects a true PMT and distinguishes such from a fast sinus rhythm, or other non-PMT condition. Advantageously, the PMT response that is invoked once a PMT is detected is not extended indefinitely. Rather, the detection of a true PMT invokes a PMT-terminating regimen calculated to terminate the PMT as rapidly as possible without any possibility of indefinitely slowing the heart rate down to dangerously low rates.

It is also seen that the invention provides a technique or method for clearly recognizing and responding to the occurrence of a true PMT without interfering with the normal operation of the pacemaker. This technique thus allows the pacemaker to perform its intended function (e.g., of providing stimulation pulses on demand) regardless of whether the pacemaker responsible for the PMT is a rate-responsive pacemaker or a fixed (programmable) rate pacemaker.

While the invention herein disclosed has been described by means of specific embodiments and applications thereof, numerous modifications and variations could be made thereto by those skilled in the art without departing from the scope of the invention set forth in the claims.

What is claimed is:

1. A system for detecting the occurrence of a pacemaker mediated tachycardia (PMT) in a patient having an implantable pacemaker, said system comprising:
    first detection means within said implantable pacemaker for detecting a prescribed sequence of cardiac cycles, each cardiac cycle of said prescribed sequence comprising a P-wave followed by a V-pulse at a rate faster than a reference rate, the time interval between said P-wave and said V-pulse of each cardiac cycle comprising a P-V delay;
    means for momentarily changing said P-V delay in a selected cardiac cycle; and
    second detection means for detecting if a V-P interval associated with said selected cardiac cycle remains substantially unchanged from a V-P interval associated with at least one cardiac cycle immediately preceding said selected cardiac cycle, said V-P interval comprising the time interval between a V-pulse and a P-wave within a cardiac cycle;
    a substantially unchanged V-P interval within said changed cardiac cycle providing an indication that said prescribed sequence of cardiac cycles comprises a PMT.

2. The system for detecting a PMT as set forth in claim 1 wherein said means for momentarily changing said P-V interval changes the P-V interval for only one cardiac cycle.

3. The system for detecting a PMT as set forth in claim 2, wherein said first detection means includes means for determining whether the heart rate of at least two consecutive cycles of said prescribed sequence of cardiac cycles is greater than said reference heart rate before said momentary changing means changes the P-V interval of said one cardiac cycle.

4. The system for detecting a PMT as set forth in claim 3, wherein said first detection means includes means for determining whether the heart rate of at least two but no more than ten consecutive cardiac cycles of said prescribed sequence of cardiac cycles is greater than said reference heart rate before said momentary changing means changes the P-V interval of said one cardiac cycle.

5. The system for detecting a PMT as set forth in claim 2, wherein said means for momentarily changing said P-V delay comprises means for increasing said P-V delay for one cardiac cycle by a prescribed amount.

6. The system for detecting a PMT as set forth in claim 5, wherein said prescribed amount comprises a time interval ranging from 40 to 60 milliseconds.

7. The system for detecting a PMT as set forth in claim 2, wherein said means for momentarily changing said P-V delay comprises means for decreasing said P-V delay for one cardiac cycle by a prescribed amount.

8. The system for detecting a PMT as set forth in claim 7, wherein said prescribed amount comprises a time interval ranging from 40 to 60 milliseconds.

9. The system for detecting a PMT as set forth in claim 1, wherein said second detection means includes means for determining if the V-P interval immediately following the changed P-V interval does not change more than approximately 30 milliseconds from the V-P interval of the at least one cardiac cycle immediately preceding said changed P-V interval.

10. The system for detecting a PMT as set forth in claim 1, wherein said momentary changing means comprises
    means for changing the P-V delay included within a first cardiac cycle by a first prescribed amount, said first cardiac cycle commencing with a first V-pulse followed by a first P-wave and concluding with a second V-pulse, said first cardiac cycle thereby including a V-P interval portion and a P-V interval portion, the V-P interval portion comprising the interval between said first V-pulse and said first P-wave, and the P-V interval portion comprising said changed P-V delay;
    a second cardiac cycle overlapping said first cardiac cycle, said second cardiac cycle commencing with said first P-wave followed by said second V-pulse and concluding with a second P-wave, said second cardiac cycle thereby including a P-V interval portion and a V-P interval portion, the P-V interval portion comprising said changed P-V delay, and the V-P interval portion comprising the interval between said second V-pulse and said second P-wave;
    said changed P-V delay thereby being included in both said first and second cardiac cycles, said first cardiac cycle including a V-P interval immediately preceding said changed P-V delay, and said second cardiac cycle including a V-P interval immediately following said changed P-V delay.

11. The system for detecting a PMT as set forth in claim 10, wherein said second detection means comprises:
    means for measuring a V-V time interval associated with said first cardiac cycle, said V-V time interval comprising the time interval between said first V-pulse and said second V-pulse;
    means for measuring a P-P time interval associated with said second cardiac cycles, said P-P time interval comprising the time interval between said first P-wave and said second P-wave;
    means for determining if the difference between said V-V time interval and said P-P time interval is less than a prescribed difference;
    a difference between said V-V time interval and said P-P time interval that is less than said prescribed difference providing an indication that the V-P interval of said first cardiac cycle has remained substantially unchanged from the V-P interval of said second cardiac cycle, and hence that said prescribed sequence of cardiac cycles comprises a PMT.

12. The system for detecting a PMT as set forth in claim 11, wherein said prescribed difference comprises approximately 35 milliseconds.

13. The system for detecting a PMT as set forth in claim 12, wherein said prescribed difference comprises approximately 25 milliseconds.

14. The system for detecting a PMT as set forth in claim 11, wherein said momentary changing means changes said P-V delay for only said first and second cardiac cycles, and thereafter returns said P-V delay to its original value.

15. The system for detecting a PMT as set forth in claim 14, wherein said momentary changing means increases said P-V delay of said first cardiac cycle by an amount ranging from 30-70 milliseconds.

16. The system for detecting a PMT as set forth in claim 15, wherein the amount of increase of said P-V delay comprises approximately 50 milliseconds.

17. The system for detecting a PMT as set forth in claim 11 further including PMT terminating means within said pacemaker for invoking a PMT termination routine upon the detection of a PMT.

18. The system for detecting a PMT as set forth in claim 17, wherein said PMT termination routine is invoked for only a single cardiac cycle upon the initial detection of a first PMT.

19. The system for detecting a PMT as set forth in claim 18, wherein said PMT termination routine is invoked for only two consecutive cardiac cycles upon the detection of a second PMT immediately subsequent to the detection of said first PMT.

20. The system for detecting a PMT as set forth in claim 17, wherein said PMT termination routine includes extending an atrial refractory period by a first prescribed amount.

21. A system for detecting the occurrence of a pacemaker mediated tachycardia (PMT) in a patient having an implantable pacemaker, said system comprising:
tachycardia detection means for detecting a tachycardia condition in a heart of said patient, said heart having atria and ventricles, said tachycardia condition comprising a plurality of consecutive cardiac cycles that exceed a prescribed rate, each cardiac cycle of said tachycardia condition including a P-wave followed by a V-pulse, the occurrence of said P-wave evidencing a non-paced contraction of the atria, and the occurrence of said V-pulse evidencing a paced contraction of the ventricles, said paced contraction of the ventricles resulting from application of said V-pulse to one of said ventricles, said V-pulse being generated by said pacemaker upon a failure of said pacemaker to sense a natural contraction of the ventricles within a prescribed P-V delay subsequent to sensing said P-wave;
modifying means responsive to said tachycardia detection means for modifying said P-V delay for a fixed number of cardiac cycles upon the detection of said tachycardia condition, whereby each of said fixed number of cardiac cycles includes a modified P-V delay; and
comparison means for comparing if a second V-P interval occurring after said modified P-V delay remains substantially unchanged relative to a first V-P interval occurring before said modified P-V delay, a V-P interval comprising the time interval between a V-pulse and the subsequent occurrence of a P-wave;
a substantially unchanged second V-P interval relative to said first V-P interval providing an indication that said tachycardia condition comprises a PMT.

22. The system for detecting a PMT as set forth in claim 21, wherein said tachycardia detection means comprises means for measuring a V-V interval and comparing said interval to a reference interval, said V-V interval comprising the elapsed time interval between V-pulses of consecutive cardiac cycles, said tachycardia condition being indicated if a prescribed number of consecutive cardiac cycles all have a V-V interval less than said reference interval.

23. The system for detecting a PMT as set forth in claim 22, wherein said prescribed number of consecutive cardiac cycles having a V-V interval less than said reference interval comprises a number from two to ten.

24. The system for detecting a PMT as set forth in claim 21, wherein said fixed number of cardiac cycles during which said P-V delay is modified by said modification means comprises one.

25. The system for detecting a PMT as set forth in claim 24, wherein said modification means comprises:
means for modifying the P-V delay included within a first cardiac cycle by a first prescribed amount, said first cardiac cycle commencing with a first V-pulse followed by a first P-wave and concluding with a second V-pulse, said first cardiac cycle thereby including a V-P interval portion and a P-V interval portion, the V-P interval portion comprising said first V-P interval compared by said comparison means, and the P-V interval portion comprising said modified P-V delay;
a second cardiac cycle overlapping said first cardiac cycle, said second cardiac cycle commencing with said first P-wave followed by said second V-pulse and concluding with a second P-wave, said second cardiac cycle thereby including a P-V interval portion and a V-P interval portion, the P-V interval portion comprising said modified P-V delay, and the V-P interval portion comprising said second V-P interval compared by said comparison means;
said modified P-V delay thereby being included in both said first and second cardiac cycles.

26. The system for detecting a PMT as set forth in claim 25, wherein said comparison means comprises:
means for measuring a V-V time interval associated with said first cardiac cycle, said V-V time interval comprising the time interval between said first V-pulse and said second V-pulse, said V-V time interval including said modified P-V delay;
means for measuring a P-P time interval associated with said second cardiac cycle, said P-P time interval comprising the time interval between said first P-wave and said second P-wave, said P-P time interval also including said modified P-V delay;
means for determining if said V-V time interval and said P-P time interval differ by an amount less than a prescribed difference;
a difference between said V-V time interval and said P-P time interval less than said prescribed difference providing an indication that the second V-P interval has remained substantially unchanged relative to the first V-P interval, and hence that the tachycardia condition comprises a PMT.

27. The system for detecting a PMT as set forth in claim 26, wherein said prescribed difference comprises approximately 25 milliseconds.

28. The system for detecting a PMT as set forth in claim 26, wherein said modifying means increases said P-V delay for approximately 50 milliseconds.

29. The system for detecting a PMT as set forth in claim 26 further including PMT terminating means within said pacemaker for invoking a PMT termination routine upon the detection of a PMT.

30. The system for detecting a PMT as set forth in claim 29, wherein said PMT termination routine is invoked for only a single cardiac cycle upon the initial detection of a first PMT.

31. The system for detecting a PMT as set forth in claim 30, wherein said PMT termination routine is invoked for only two consecutive cardiac cycles upon the detection of a second PMT immediately subsequent to the detection of said first PMT.

32. The system for detecting a PMT as set forth in claim 29, wherein said PMT termination routine includes extending an atrial refractory period by a first prescribed amount.

33. A method for detecting a PMT in a patient having an implanted pacemaker, said method comprising the steps of:
(a) sensing a P-wave followed by a V-pulse in a plurality of successive cardiac cycles;
(b) sensing if the plurality of successive cardiac cycles sensed in step (a) occurs at a rate in excess of a tachycardia reference rate (TRR);
(c) increasing a P-V delay in a single cardiac cycle when the rate of the plurality of successive cardiac cycles sensed in step (b) exceeds the TRR;
(d) measuring a V-V time interval associated with said single cardiac cycle, said V-V time interval comprising the elapsed time between a first V-pulse and a second V-pulse, a first P-wave occurring after the first V-pulse and prior to the second V-pulse, the increased P-V delay of step (c) being included in the V-V time interval as the time interval between the first P-wave and the second V-pulse;
(e) measuring a P-P time interval associated with said single cardiac cycle, said P-P time interval comprising the elapsed time between said first P-wave and a second P-wave, said second P-wave occurring after the second V-pulse, the increased P-V delay of step (c) being included in the P-P time interval as the time interval between the first P-wave and the second V-pulse;
(f) measuring the difference between said V-V time interval and said P-P time interval; and
(g) indicating a PMT condition when the difference between said V-V time interval and said P-P time interval is less than a prescribed difference.

34. The method for indicating a PMT in a patient as set forth in claim 33, wherein step (c) includes increasing said P-V delay by an amount within the range of 40 to 70 milliseconds.

35. The method for indicating a PMT in a patient as set forth in claim 34, wherein step (c) includes increasing said P-V delay by approximately 50 milliseconds.

36. The method for indicating a PMT in a patient as set forth in claim 33, wherein step (g) includes indicating said PMT condition when the difference between said V-V interval and said P-P interval comprises a difference less than about 35 milliseconds.

37. The method for indicating a PMT in a patient as set forth in claim 36, wherein step (g) includes indicating said PMT condition when the difference between said V-V interval and said P-P interval comprises a difference less than 25 milliseconds.

38. The method for indicating a PMT in a patient as set forth in claim 33 further including:
(h) automatically invoking a PMT termination routine in response to the indication of a PMT condition in step (g), said PMT termination routine being generated by said pacemaker.

39. The method for indicating a PMT in a patient as set forth in claim 38, wherein step (h) includes invoking said PMT termination routine for only a single cardiac cycle upon an initial indication of a PMT condition.

40. The method for indicating a PMT in a patient as set forth in claim 39 further including invoking said PMT termination routine for one additional consecutive cardiac cycle upon sensing an R-wave without first sensing an atrial event immediately following a first indication of a PMT condition.

* * * * *